United States Patent
Keogh et al.

(10) Patent No.: US 6,447,443 B1
(45) Date of Patent: Sep. 10, 2002

(54) METHOD FOR ORGAN POSITIONING AND STABILIZATION

(75) Inventors: James R. Keogh, Maplewood, MN (US); Scott E. Jahns, Hudson, WI (US); Michael A. Colson, Chanhassen, MN (US); Gary W. Guenst, Collegeville, PA (US); Christopher Olig, Eden Prairie, MN (US); Paul A. Pignato, Stacy, MN (US); Karen Montpetit, Mendota Heights, MN (US); Thomas Daigle, Corcoran, MN (US); Douglas H. Gubbin, Brooklyn Park, MN (US); William G. O'Neill, Maple Grove, MN (US); Katherine Jolly, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/879,294

(22) Filed: Jun. 12, 2001

Related U.S. Application Data

(60) Provisional application No. 60/286,952, filed on Apr. 26, 2001, provisional application No. 60/282,029, filed on Apr. 6, 2001, provisional application No. 60/263,739, filed on Jan. 24, 2001, and provisional application No. 60/261,343, filed on Jan. 13, 2001.

(51) Int. Cl.$^7$ .............................. A61F 2/00; A61B 1/32; A61B 19/00
(52) U.S. Cl. ..................... 600/37; 600/205; 600/235; 600/232; 128/898
(58) Field of Search .................. 600/37, 201, 205, 600/235, 232; 606/1; 128/898; 607/2, 4, 7, 9

(56) References Cited

U.S. PATENT DOCUMENTS

| | | | |
|---|---|---|---|
| 4,832,048 A | 5/1989 | Cohen ........................ 128/786 |
| 5,254,600 A | 10/1993 | Blanpied et al. ............. 521/125 |
| 5,387,234 A | 2/1995 | Hirschberg .................. 607/129 |
| 5,423,878 A | 6/1995 | Franz .......................... 607/122 |
| 5,451,223 A | 9/1995 | Ben-Simhon ................ 606/42 |
| 5,553,612 A | 9/1996 | Lundbäck .................... 128/643 |
| 5,571,088 A | 11/1996 | Lennox et al. ................ 604/96 |
| 5,575,772 A | 11/1996 | Lennox ........................ 604/96 |
| 5,651,378 A * | 7/1997 | Matheny et al. ............. 128/898 |
| 5,803,911 A | 9/1998 | Inukai et al. ................ 600/387 |
| 5,836,311 A | 11/1998 | Borst et al. .................. 128/897 |
| 5,891,028 A | 4/1999 | Lundbäck .................... 600/387 |
| 5,904,711 A | 5/1999 | Flom et al. .................. 607/129 |
| 5,913,876 A * | 6/1999 | Taylor et al. ................... 607/2 |
| 5,927,284 A | 7/1999 | Borst et al. .................. 128/898 |
| 6,004,269 A | 12/1999 | Crowley et al. ............. 600/439 |
| 6,006,138 A | 12/1999 | Michael ....................... 607/124 |
| 6,015,378 A | 1/2000 | Borst et al. .................... 600/37 |
| 6,063,081 A | 5/2000 | Mulier et al. .................. 606/45 |
| 6,064,901 A | 5/2000 | Cartmell et al. ............. 600/372 |
| 6,238,334 B1 | 5/2001 | Easterbrook, III et al. ..... 600/16 |
| 6,254,525 B1 | 7/2001 | Reinhardt et al. ............ 600/17 |
| 2002/0045795 A1 * | 4/2002 | Aboul-Hosn et al. ......... 600/16 |

\* cited by examiner

*Primary Examiner*—Jeffrey A. Smith
(74) *Attorney, Agent, or Firm*—Thomas G. Berry; Daniel W. Latham

(57) ABSTRACT

This invention provides a system and method for positioning, manipulating, holding, grasping, immobilizing and/or stabilizing a heart including one or more tissue-engaging devices, one or more suction sources, one or more fluid sources, one or more energy sources, one or more sensors and one or more processors. The system and method may include an indifferent electrode, a drug delivery device and an illumination device. The system's tissue-engaging device may comprise a tissue-engaging head, a support apparatus and a clamping mechanism for attaching the tissue-engaging device to a stable object. The system may be used during various medical procedures including the deployment of an anastomotic device, intermittently stopping and starting of the heart, ablation of cardiac tissues and the placement of cardiac leads.

16 Claims, 23 Drawing Sheets

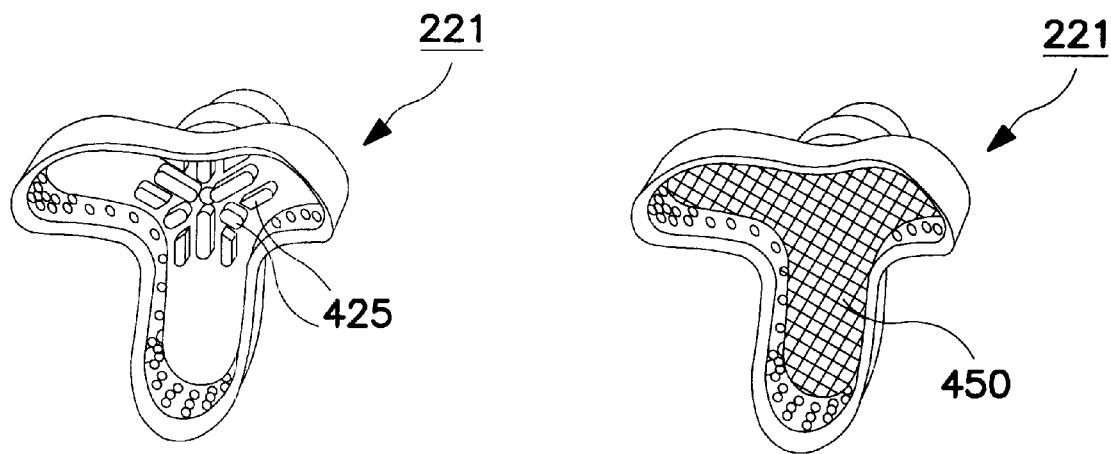
FIG. 11
FIG. 12
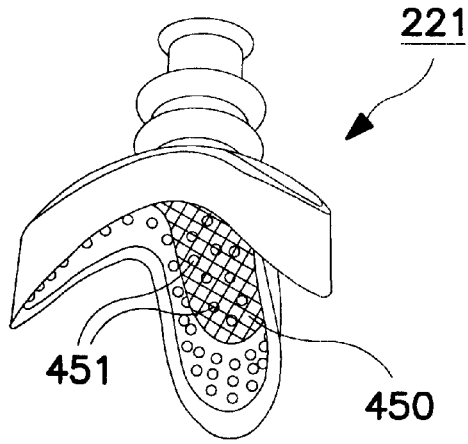
FIG. 13
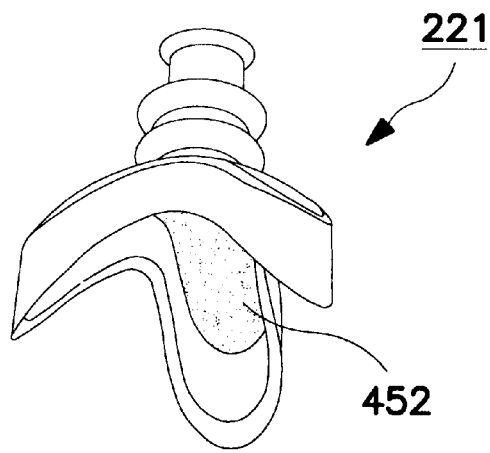
FIG. 14

METHOD FOR ORGAN POSITIONING AND STABILIZATION

CROSS-REFERENCE TO RELATED APPLICATION

This application claims priority to co-owned U.S. Provisional Patent Applications Serial No. 60/261,343 filed Jan. 13, 2001, Serial No. 60/263,739 filed Jan. 24, 2001, Serial No. 60/282,029 filed Apr. 6, 2001 and Serial No. 60/286,952 filed Apr. 26, 2001, the disclosures of which are incorporated herein by reference.

FIELD OF THE INVENTION

This invention relates generally to a system and method for positioning an organ, and more particularly to a system capable of positioning, manipulating, stabilizing and/or holding a heart during cardiac surgery. This invention also relates to a positioning system and method that includes monitoring one or more chemical, physical or physiological characteristics of a bodily tissue or fluid during a medical procedure.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft (CABG) procedure. CABG surgery, also known as "heart bypass" surgery, generally entails the use of a graft or conduit to bypass the coronary obstruction and, thereby provide blood flow to the downstream ischemic heart tissues. The procedure is generally lengthy, traumatic and subject to patient risk. Among the risk factors involved is the use of a cardiopulmonary bypass (CPB) circuit, also known as a "heart-lung machine", to both pump blood and oxygenate the blood so that the patient's heart may be stopped during the surgery, with its function performed by the CPB circuit.

Conventional CABG procedures are typically conducted on an arrested heart while the patient is on CPB. The CPB circuit provides continuous systemic blood circulation, while cardioplegic cardiac arrest enables meticulous anastomosis suturing in a bloodless, still operative field. In the majority of patients, obstructed coronary arteries are bypassed; for example, with an in situ internal mammary artery (IMA) or a reversed segment of saphenous vein harvested from a leg.

Segments of other suitable blood vessels may also be used for grafting depending on availability, size and quality. In general, the body hosts seven potential arterial conduits, the right and left IMAs, the radial arteries and three viceral arteries, one in the abdomen, and two in the lower abdominal wall, though the latter may be quite short and are generally of limited usefulness. The viceral arteries include the gastroepiploic artery and the splenic artery.

The left IMA is best used for bypass to the left anterior descending (LAD) coronary artery and its diagonal branches. Whereas, the right IMA may be used for bypass to selected vessels more posterior such as the distal right coronary artery (RCA). The right IMA may also be used for bypass to selected marginal branches of the left circumflex coronary artery. A segment of radial artery harvested from an arm is generally used to revascularize the posterior surface of the heart. The right gastroepiploic artery may be used to revascularize almost any artery on the surface of the heart. It is most commonly used for bypass to the distal RCA or the posterior descending coronary artery. In unusual circumstances the splenic artery is used to revascularize posterior coronary arteries, but it is long enough to reach the marginal branches of the circumflex coronary artery.

Surgeons will generally complete bypass grafts to the following coronary arteries in a patient undergoing multiple bypass surgery in roughly the following order: posterior descending coronary artery (PDA), RCA, obtuse marginal branch, circumflex coronary artery, diagonal branch, and LAD. More generally, surgeons will revascularize the three coronary systems in the following order: right, circumflex, and anterior descending. However, the order may vary depending on whether the procedure is performed on a beating heart or an arrested heart. For arrested heart, about 3 to 4 bypass grafts of which 1 to 3 are free grafts are generally performed per procedure. In contrast, about 2 to 3 bypass grafts of which 0 to 2 are free grafts are generally performed per beating heart procedure. In general, 1 free graft is used per beating heart procedure.

When a saphenous vein or other blood vessel is used as a free graft in a procedure, two anastomoses are performed; one to the diseased artery distal to the obstruction (outflow end), and one proximally to the blood vessel supplying the arterial blood (inflow end). These anastomoses are generally performed using end-to-side anastomotic techniques. Rarely an end-to-end anastomotic technique is used. When more than one graft is required in any of the three coronary systems for complete revascularization of the heart, sequential graft techniques may be used to conserve the amount of blood vessels required. Sequential graft techniques use proximal side-to-side anastomoses and an end-to-side anastomosis to complete the graft. For example, a common sequence used in the anterior descending coronary system is a side-to-side anastomosis of graft to the diagonal branch and an end-to-side anastomosis of graft to the LAD coronary artery. However, only a small percentage of anastomoses are side-to-side anastomoses.

The majority of surgeons will complete the distal anastomosis of a graft prior to completion of the proximal anastomosis. The small percentage of surgeons who do complete the proximal anastomosis first usually do so to allow antegrade perfusion of cardioplegic solution through the graft during revascularization. Construction of the distal anastomosis, e.g., a saphenous vein-coronary artery anastomosis, begins by first locating the target artery on the heart. Next, an incision is made through the epicardium and the myocardium to expose the artery. An arteriotomy is then made using a knife to incise the artery. The incision is then extended with a scissors. The length of the incision approximates the diameter of the saphenous vein, about 4 to 5 mm. The diameter of the target artery is generally 1.5 to 2.0 mm.

Since, most surgeons currently feel the distal take-off angle should be 30 to 45 degrees, the distal end of the saphenous vein is usually beveled at about 30 to 45 degrees.

Currently, surgeons generally construct the anastomosis via a ten-stitch running suture using 7-0 polypropylene suture material. The ten-stitch anastomosis typically comprises five stitches around the heel of the graft and five stitches around the toe. The five stitches around the heel of the graft comprise two stitches to one side of the apex of the graft and the artery, a stitch through the apex and two stitches placed at the opposite side of the apex. The graft is generally held apart from the coronary artery while the stitches are constructed using a needle manipulated by a forceps. Suture loops are drawn up and the suture pulled straight through to eliminate purse-string effect. The five stitches around the toe of the graft also comprises two stitches to one side of the apex of the graft and the artery, a stitch through the apex and two stitches placed at the opposite side of the apex. Again, suture loops are drawn up and the suture pulled straight through to eliminate purse-string effect. The suture ends are then tied.

The proximal anastomosis of a saphenous vein graft to the aorta, i.e., an aortosaphenous vein anastomosis, is formed by first removing the pericardial layer that covers the aorta. An occluding or side-biting clamp may be placed on the aorta at the anastomosis site or an aortotomy occlusion device may be used following creation of the aortotomy. A small circular or elliptical portion of the ascending aorta is excised forming a small opening 4 to 5 mm in diameter, i.e. the aortotomy. An aortic punch typically facilitates this procedure. The opening for a right-sided graft is made anterior or to the right lateral side of the aorta, whereas an opening for a left-sided graft is made to the left lateral side of the aorta. If the graft is to supply blood to the right coronary artery, the opening is generally made proximal on the aorta. If the graft is to supply blood to the anterior descending coronary artery, the opening is generally made in the middle on the aorta. And, if the graft is to supply blood to the circumflex artery, the opening is generally made distal on the aorta. The right graft opening is placed slightly in the right of the anterior midpoint of the aorta and the left graft opening slightly to the left. The end of the saphenous vein is cut back longitudinally for a distance of approximately 1 cm. A vascular clamp is placed across the tip of the saphenous vein to flatten it, thereby exposing the apex of the vein. Five suture loops of a running suture using 5-0 polypropylene are then placed around the 'heel' of the graft and passed through the aortic wall. Two stitches are placed on one side of the apex, the third stitch is placed precisely through the apex of the incision in the saphenous vein, and the final two stitches are placed on the opposite side of the apex. Suture traction is used to help expose the edge of the aortic opening to ensure accurate needle placement. Stitches include about 3 to 5 mm of the aortic wall for adequate strength. Suture loops are then pulled up to approximate the vein graft to the aorta. The remaining stitches are placed in a cartwheel fashion around the aortic opening thereby completing the remainder of the anastomosis.

Left-sided grafts are oriented so the apex of the incision in the "heel" of the saphenous vein will face directly to the left side. The stitches are placed in a clockwise fashion around the heel of the graft and in a counterclockwise fashion around the aortic opening. Right-sided grafts are oriented in a caudal fashion. The stitches are placed in a counterclockwise fashion around the heel of the graft and in a clockwise fashion around the aortic opening. Five suture loops complete the heel portion of the graft and an additional five or six are necessary to complete the toe of the graft. Finished proximal anastomoses typically have a "cobrahead" appearance.

It is essential for the surgeon to take steps to minimize the possibility of thrombosis, narrowing and/or premature closure of the anastomosis due to technical errors. Some surgeons feel the proximal anastomosis must have a take-off angle of 45 degrees while other surgeons believe the take-off angle is not critical. In addition, it was felt that intima-to-intima contact of the vessels at the anastomosis was critical for endothelization to occur, thereby making an ideal union of the vessels. However, most surgeons now feel intima-to-adventitia contact is acceptable. The main objective of the surgeon is to create an anastomosis with an expected long-term patency rate of greater than 5 to 10 years. The creation of an anastomosis currently takes approximately 10–15 minutes.

One essential requirement for creating an anastomosis without error is adequate exposure of the target vessel. Acute visualization of the vessel walls is mandatory in order to properly place each stitch and avoid inadvertently including the back wall of the vessel in a stitch, which in effect narrows or completely occludes the vessel. In order to achieve the required exposure most surgeons will employee blood-less field devices such as shunts, snares, and misted blowers. Further, largely invasive surgical techniques are also employed to help the surgeon gain access to the grafting site. For this reason, CABG surgery is typically performed through a median sternotomy, which provides access to the heart and to all major coronary branches. A median sternotomy incision begins just below the sternal notch and extends slightly below the xiphoid process. A sternal retractor is used to spread the left and right rib cage apart for optimal exposure of the heart. Hemostasis of the sternal edges is typically obtained using electrocautery with a ball-tip electrode and a thin layer of bone wax. The pericardial sac is opened thereby achieving direct access to the heart.

A blood vessel or vessels for use in the graft procedure are mobilized from the patient. This usually entails mobilizing either a mammary artery or a saphenous vein, although other graft vessels as discussed above may also be used. A heart-lung or cardiopulmonary bypass is performed. This usually entails arterial and venous cannulation, connecting the bloodstream to a heart-lung machine, cooling the body to about 32 degrees Celsius, cross clamping of the aorta and cardioplegic perfusion of the coronary arteries to arrest and cool the heart to about 4 degrees Celsius. A proximal anastomosis may be performed on partial bypass using a partial occluding aortic cross-clamp or side-clamp. The arrest or stoppage of the heart is generally required because the constant pumping motion of the beating heart would make surgery upon the heart difficult in some locations and extremely difficult if not impossible in other locations Once cardiac arrest is achieved, then a graft (or grafts) is attached to the relevant portions of a coronary artery (or arteries) followed by weaning from the cardiopulmonary bypass, restarting the heart and decannulation. Finally the chest is closed.

Problems that may be associated with conventional CABG procedures with CPB include the initiation of a systemic inflammatory response due to the interactions of blood elements with the artificial material surfaces of the CPB circuit. Global (hypothermic) cardiac arrest may result in global myocardial ischemia and cross clamping the ascending aorta may contribute to the patient experiencing a post-operative stroke. In fact, recent studies have shown aortic clamping and manipulation may release atherosclerotic debris into the bloodstream, resulting in neurologic injury.

Currently, the golden standard for creation of a vascular anastomosis is manual suturing. Manual suturing may be used to attach vascular grafts (either autografts or prosthetic grafts) for coronary bypass, femoral-femoral bypass (to relieve inadequate circulation in the legs), and AV fistulas and/or shunts (access portals for repeated puncture applications such as kidney dialysis or diabetes). However, a number of cardiac surgical procedures, e.g., off-pump, beating heart CABG procedures, minimally invasive procedures and even totally endoscopic procedures with access through ports only, may require a variety of new anastomotic techniques. The ability of performing anastomoses with limited or no CPB support may increase the possibility of performing more CABG procedures using minimally invasive surgical techniques. Avoiding the use of cross clamps and CPB or dramatically reducing pump run and cross clamp times may effectively minimize post-operative complications. For this reason, there is an increasing need for easier, quicker, less damaging, but reliable automated, semi-automated, or at least facilitated methods to replace or enhance the normal process of a manually sutured vascular anastomosis.

The major objective of any CABG procedure is to perform a technically perfect anastomosis. However, creation of a technically perfect anastomosis is generally complex, tedious, time consuming and its success is highly dependent on a surgeon's skill level. Therefore, creation of vascular anastomoses without the need to perform delicate and intricate suture lines may enable surgeons to more quickly create simpler and effective anastomoses. Currently, there are a number of techniques or procedures being investigated for facilitating the process of forming an anastomosis including vascular clips or staplers, glues, adhesives or sealants, laser welding, mechanical couplers, stents and robot-assisted suturing. These techniques are being developed for performing end-to-end, end-to-side and/or side-to-side anastomoses with or without temporary blood flow interruption. In general, these techniques may include the use of various biomaterials and/or biocompatible agents.

In an effort to reduce or eliminate occlusive anastomosis time, various techniques or procedures are being investigated. These procedures include coronary shunting techniques, which enable manual suturing without time-constraint due to persistent distal perfusion, and accelerated tissue-bonding techniques, e.g., tissue adhesives and laser welding. Some nonocclusive anastomosis techniques being developed require apposition of the intima of the graft to the adventitia of the recipient artery.

Sealants, adhesives or glues may be based on synthetic or biological substances or a combination of both. They are generally used to either seal post-operative internal air or fluid leaks, or to close a topical wound. Surgical sealants are generally absorbable materials used primarily to control internal bleeding and to seal tissue. Surgical adhesives, stronger than sealants, are often non-absorbable, but tend to be biologically based. Surgical glues, stronger than adhesives, are often synthetic and non-absorbable. In addition, glues are often used for topical wounds. Surgical glues are typically made from cyanoacrylates, a strong adhesive found in commercially available super glues. Biologically based sealants, adhesives or glues are generally derived from blood clotting components such as proteins (e.g., fibrinogen or fibrin), enzymes (e.g., thrombin) and/or platelets. Fibrin based sealants, adhesives or glues generally combine the protein fibrinogen with the enzyme thrombin to immediately begin the clotting process. One surgical adhesive currently being marketed includes a combination of collagen (proteins which form fibers to support body tissues), formalin (a form of formaldehyde), resorcinol and glutaraldehyde. Some sealants, adhesives or glues may be used to control bleeding or to reinforce suture or staple lines rather than to make tissues adhere, thus functioning more as hemostatic agents than glues.

There are a number of uses for sealants, adhesives or glues such as replacement for sutures and staples in minimally invasive procedures where the surgeon has little room to maneuver or for the repair of aortic dissections, where the tissue is so thin it may be damaged by sutures. They may also be used for anastomotic sealing, in which the seal should not be absorbed or carotid patching, where a complete seal is desired.

Laser welding is another potential method for forming an anastomosis. Laser welding uses lasers such as $CO_2$ lasers, argon lasers or Neodymium-YAG lasers, to join tissues together thermally instead of, for example, mechanically. One possible mechanism of laser welding of tissues is the thermal denaturation and coagulation of collagen fibrils in the tissue, which generally occur above 60° C. To improve the procedure, photosensitive dyes (e.g., indocyanine green) may be applied at the weld site to enhance light absorption and minimize thermal damage to the surrounding tissue. Using a dye that adsorbs light at a very specific frequency, a laser can be then used to selectively heat the dye and not the surrounding tissue. Photosensitive dyes used in laser welding procedures may or may not bind chemically to the tissue's proteins. Unlike sutures or staples, laser welding may offer a water tight seal to hold bodily fluids in, thereby preventing blood loss, infections and repeat surgeries. A further enhancement to the laser welding technique is to use a "solder". Solders may comprise synthetic and/or biological components. For example, proteins such as albumin have been used in various solder formulations. Typical laser welding devices include one or more flexible optical fibers and solder-delivery tubes that may be snaked through small ports or through a channel in an endoscope.

Mechanical anastomotic devices include stapling devices, clipping devices, ring and pin coupling devices and suturing devices. These anastomotic devices may be automated or semi-automated. Mechanical anastomotic devices also include mechanical couplers including stents, ferrules, and/ or rings. Materials used to form an anastomosis via a mechanical device and/or coupler may be biocompatible, bioabsorbable, bioactive and/or bioinert.

One component intra-luminal mechanical anastomotic devices are generally stent-like in design. The graft and the target vessel, i.e., the aorta or coronary artery, are forced into tubular shapes by the device. In general, the application of this type of device is relatively easy. The device can be made to unfold by itself so no deformation forces are necessary at the anastomosis. In addition, angled anastomoses are possible. The device may however have a lot of foreign material exposed within the blood stream, thus increasing the risk of stenosis and thrombosis. In some cases, the device may prevent direct contact between the graft and the target vessel, thereby preventing the vessel walls from healing together. Intimal damage to both the graft and the target vessel may also occur during delivery of the device. Extra sealing methods, e.g., tissue sealants, may be necessary to provide a leak-free anastomosis. In addition, the size of the device is strongly related to the size of the vessels. Therefore, a range of devices and measurement of the vessels is necessary.

Two component intra-luminal mechanical anastomotic devices require both the graft and the target vessel to be connected to their own coupling component, after which the two coupling components are connected to each other, thereby forming the complete anastomosis. Problems associated with construction of an anastomosis using a two component intra-luminal mechanical coupling device include mounting of the vessels and connection of the components. Tools for mounting the individual coupling components to each vessel and tools for connecting the coupling components together are both required.

One component extra-luminal mechanical anastomotic devices generally require a delivery tool to position the coupling device in the recipient vessel. One component extra-luminal mechanical coupling devices generally allow direct intima-to-intima contact. In addition, this type of device will have less foreign material in the blood stream, thereby decreasing the risk of stenosis and thrombosis. For this reason, less biological testing may be required as opposed to an intra-luminal stent-like device. However, mounting of the graft to the coupling device may not be easy. Damage may occur due to everting of the graft onto the device. For example, everting of a graft onto a device may cause damage to the intimal layer. This damage may occur for two reasons: 1) solid grabbing of the vessel wall is necessary to evert an artery, thus one tip of the pair of pincers will roughly touch the intima; and, 2) eversion causes high strain (stretching), which will damage the arteries. Another problem is that skills are still necessary for proper eversion. The surgeon has to estimate where to grab the vessel wall and how to lift it over one of the pins to obtain a symmetrical anastomosis. A specially designed mounting tool may make the step of mounting the graft onto the coupling device easier and may help to minimize damage to the graft. In addition, care must be taken to avoid compression of tissue by the coupling device since compression can cause pressure necrosis.

Two component extra-luminal mechanical anastomotic devices, like the two component intra-luminal mechanical coupling devices, require both the graft and the target vessel to be connected to their own coupling component, after which the two coupling components are connected to each other, thereby forming the complete anastomosis. Problems associated with construction of an anastomosis using a two component extra-luminal mechanical coupling device also include mounting of the vessels and connection of the components. Tools for mounting the individual coupling components to each vessel and tools for connecting the coupling components together may be required.

Hybrid anastomosis techniques combine one or more techniques, e.g., sutures or clips with glues or laser welding. A specific example of a hybrid anastomotic technique is the use of an intraluminal stent like device combined with an extraluminal application of biological glue.

One area which may create difficulties for the patient and extra expense and time for a stopped heart CABG procedure involves CPB. In a CPB procedure all the patient's blood, which normally returns to the right atrium, is diverted to a system which supplies oxygen to the blood and removes carbon dioxide from the blood and returns the blood, at sufficient pressure, into the patient's aorta for further distribution into the body. Generally such a system requires several separate components, including an oxygenator, several pumps, a reservoir, a blood temperature control system, filters as well as flow, pressure and temperature sensors.

Problems may develop during cardiopulmonary bypass due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during cardiopulmonary bypass, others have attempted to perform a coronary artery bypass graft procedure without cardiac arrest and cardiopulmonary bypass. For example, Trapp and Bisarya in "Placement of Coronary Artery Bypass Graft Without Pump Oxygenator", Annals Thorac. Surg. Vol. 19, No. 1, (January 1975) pgs. 1–9, immobilized the area of the bypass graft by encircling sutures deep enough to incorporate enough muscle to suspend an area of the heart and prevent damage to the coronary artery. More recently Fanning et al. in "Reoperative Coronary Artery Bypass Grafting Without Cardiopulmonary Bypass", Annals Thorac. Surg. Vol. 55, (February 1993) pgs. 486–489 also reported immobilizing the area of the bypass graft with stabilization sutures.

Suction stabilization systems, such as the Medtronic Octopus® Tissue Stabilizer and Accessories (available from Medtronic, Inc., Minneapolis, Minn. USA), the current model being designated the "Octopus 3™ stabilization system", use suction to grip and immobilize the surface of the heart. Additionally, the system allows the surgeon to manipulate the anastomosis site into better view by rotating and supporting the heart. See, also, e.g., U.S. Pat. Nos. 5,836,311; 5,927,284 and 6,015,378, and co-assigned U.S. patent applications Ser. No. 09/396,047, filed Sep. 15, 1999, Ser. No. 09/559,785, filed Apr. 27, 2000, and Ser. No. 09/678,203, filed Oct. 2, 2000; and European Patent Publication No. EP 0 993 806. The Octopus™ stabilizer facilitates moving or repositioning the heart to achieve better access to areas which would otherwise be difficult to access, such as the posterior or backside of the heart.

It would be desirable to have an organ positioning system and method that comprises a device that engages organ tissue and allows a surgeon to easily position, manipulate, stabilize and/or hold an organ during a medical procedure.

It would further be desirable to have an organ positioning system and method that comprises a device that engages organ tissue and allows a surgeon to easily position, manipulate, stabilize and/or hold an organ during an ablation procedure.

It would be desirable to have an organ positioning system and method that comprises a device that engages organ tissue and allows a surgeon to easily position, manipulate, stabilize and/or hold an organ during an anastomotic procedure.

It would be desirable to have an organ positioning system and method that comprises a device that engages organ tissue and allows a surgeon to easily position, manipulate, stabilize and/or hold an organ during a controlled intermittent asystole procedure.

It would further be desirable to have an organ positioning system and method that comprises a device that engages organ tissue and allows a surgeon to easily position, manipulate, stabilize and/or hold organ tissue during a medical procedure, thereby providing adequate exposure, e.g., adequate visualization and/or access, to a surgical site.

It would further be desirable to have an organ positioning system and method that allows the organ, for example, heart to be positioned in a desired orientation but otherwise allowing movement of the heart as the heart beats.

It would further be desirable to have an organ positioning system and method that is designed to be relatively atraumatic to tissue.

It would further be desirable to have an organ positioning system and method which is capable of positioning, manipulating, stabilizing and/or holding an organ and/or tissue while controllably monitoring one or more chemical, physical or physiological characteristics of a bodily tissue or fluid during a medical procedure.

It would further be desirable to have an organ positioning system and method which is capable of positioning an organ and/or tissue while controllably providing suction during a medical procedure.

It would further be desirable to have an organ positioning system and method which is capable of positioning, manipulating, stabilizing and/or holding an organ and/or tissue while controllably providing fluid during a medical procedure.

It would further be desirable to have an organ positioning system and method which is capable of positioning, manipulating, stabilizing and/or holding an organ and/or tissue while controllably providing energy during a medical procedure.

It would further be desirable to have an organ positioning system and method which is capable of positioning, manipulating, stabilizing and/or holding an organ and/or tissue while controllably providing illumination during a medical procedure.

SUMMARY OF THE INVENTION

One aspect of the present invention provides a system for positioning, manipulating, holding, grasping, immobilizing and/or stabilizing an organ, such as a heart. The system may include one or more tissue-engaging devices, one or more suction sources, one or more fluid sources, one or more energy sources, one or more sensors and one or more processors. The system may also include an indifferent electrode, a drug delivery device and/or an illumination device. A tissue-engaging device of the system may comprise a tissue-engaging head, a support apparatus and a clamping mechanism for attaching the tissue-engaging device to a stable object, such as a retractor that is fixed to a patient's chest. A tissue-engaging device of the system may comprise one or more energy transfer elements connected to an energy source, one or more sensors connected to a processor, one or more suction openings connected to a suction source, and/or one or more fluid openings connected to a fluid source.

Another aspect of the present invention provides a method of positioning, manipulating, holding, grasping, immobilizing and/or stabilizing an organ, such as a heart. The method includes engaging and positioning an organ, such as a heart, during a medical procedure. The medical procedure may include deployment of one or more anastomotic devices, e.g., during a CABG procedure. The medical procedure may include intermittently stimulating a vagal nerve and pacing a heart. The medical procedure may include ablating one or more tissues of a heart. The medical procedure may include placement of a lead on or within a heart. The method may include the use of suction to engage and position an organ, such as a heart.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

BRIEF DESCRIPTION OF THE DRAWINGS

FIG. 11 is a bottom view of one embodiment of a tissue-engaging head of a medical device in accordance with the present invention.

FIG. 12 is a bottom view of one embodiment of a tissue-engaging head of a medical device in accordance with the present invention.

FIG. 13 is a side view of one embodiment of a tissue-engaging head of a medical device in accordance with the present invention.

FIG. 14 is a side view of one embodiment of a tissue-engaging head of a medical device in accordance with the present invention.

DETAILED DESCRIPTION OF THE PRESENTLY PREFERRED EMBODIMENTS

Figure 1:
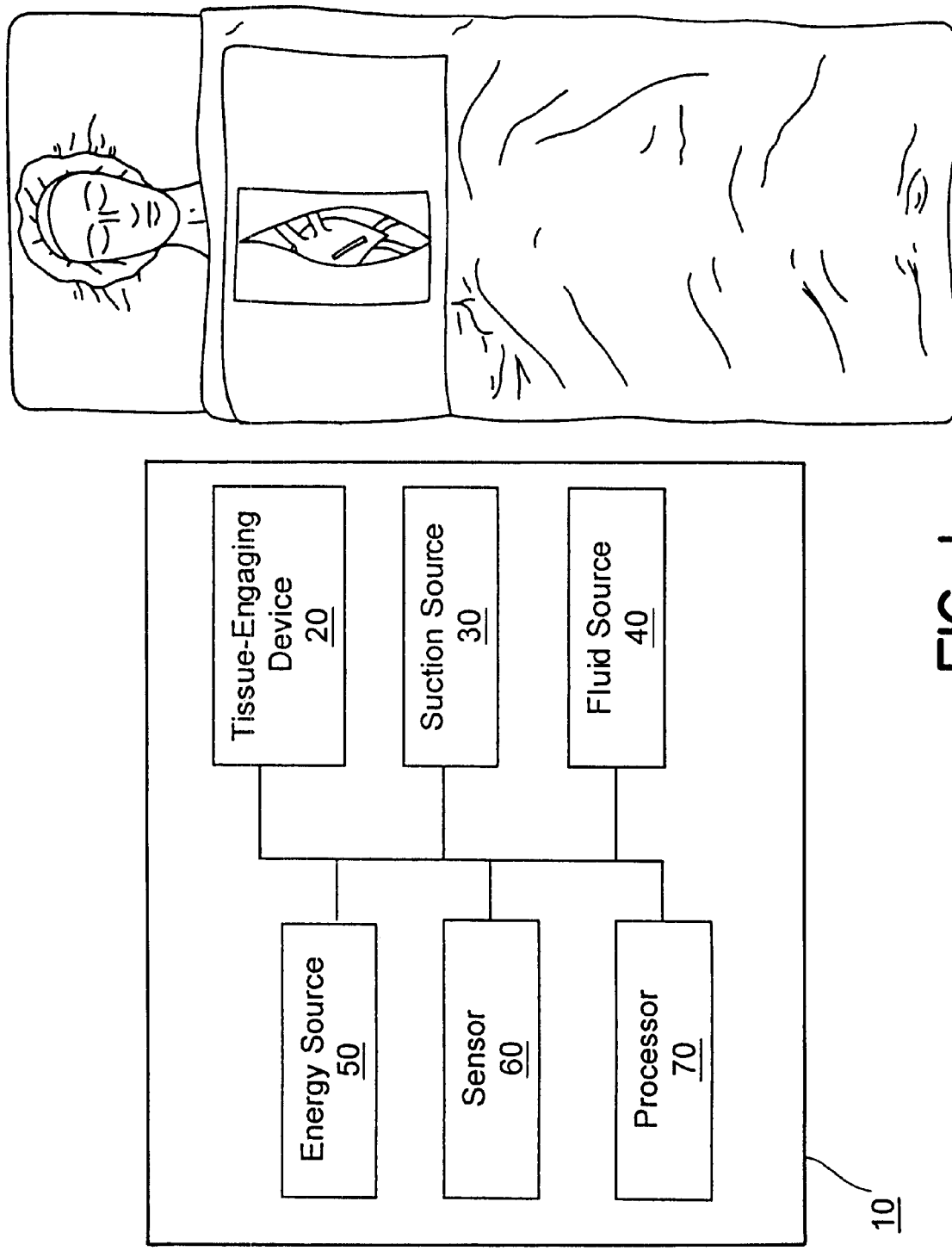
FIG. 1 is a schematic view of one embodiment of a system in accordance with the present invention.

FIG. 1 shows a schematic view of one embodiment of system 10 for positioning, manipulating, holding, grasping, immobilizing and/or stabilizing tissue in accordance with the present invention. In this embodiment, system 10 is shown to comprise tissue-engaging device 20, a suction source 30, a fluid source 40, an energy source 50, a sensor 60 and a processor 70. System 10 may also include an indifferent electrode, a drug delivery device and/or an illumination device (all not shown in FIG. 1). The indifferent electrode may be placed on the patient's body such as the back, thigh or shoulder or another site other than the suction site. The drug delivery device may be used to deliver drugs to a patient. The illumination device may be used to illuminate a surgical site.

Figure 2:
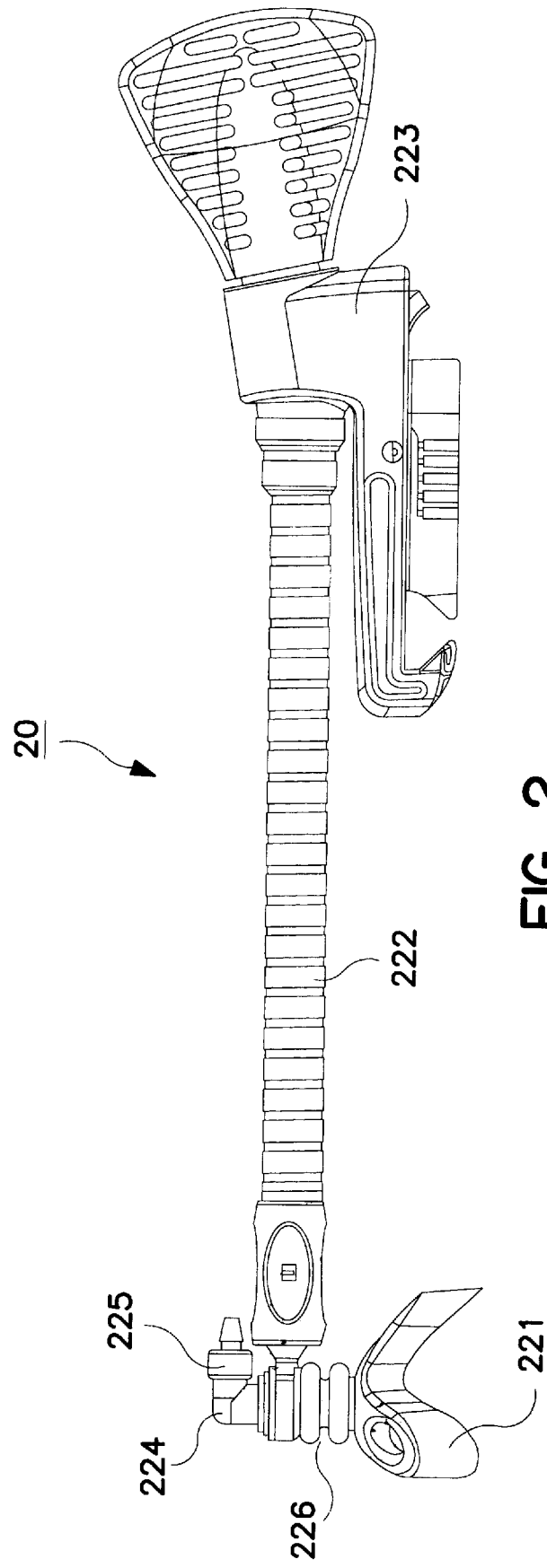
FIG. 2 is a side view of one embodiment of a medical device in accordance with the present invention.

As shown in FIG. 2, in one embodiment of the present invention, tissue-engaging device 20 may comprise a tissue-engaging head 221, a support apparatus 222 and a clamping mechanism 223 for attaching device 20 to a stable structure, such as a retractor (not shown in FIG. 2), that is fixed to a patient. Tissue-engaging device 20 may also comprise one or more energy transfer elements, one or more connectors for connecting the one or more energy transfer elements to energy source 50, one or more sensing elements, one or more connectors for connecting the one or more sensing elements to sensor 60, one or more suction openings, one or more conduits for providing suction from suction source 30 to the one or more suction openings, one or more fluid openings, one or more conduits for providing fluid from fluid source 40 to the one or more fluid openings, and/or one or more connectors for connecting one or more components of tissue-engaging device 20 to processor 70.

Tissue-engaging device 20 and its components are preferably made of one or more biocompatible materials. Biocompatible materials or biomaterials are usually designed and constructed to be placed in or onto tissue of a patient's body or to contact fluid of a patient's body. Ideally, a biomaterial will not induce undesirable reactions in the body such as blood clotting, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains in contact with tissues or fluids of the body.

Materials that are either biocompatible or may be modified to be biocompatible and may be used to make suction device 20 may include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, dacron, minerals or ceramics such as hydroxapatite, epoxies, human or animal protein or tissue such as bone, skin, teeth, collagen, laminin, elastin or fibrin, organic materials such as wood, cellulose, or compressed carbon, and other materials such as glass, and the like. Materials that are not considered biocompatible may be modified to become biocompatible by a number of methods well known in the art. For example, coating a material with a biocompatible coating may enhance the biocompatibility of that material.

One or more surfaces of tissue-engaging device 20 may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized by a variety of methods well known in the art.

Tissue-engaging device 20 may comprise a tissue-engaging head. The tissue-engaging head may be flexible thereby allowing the head to conform to the surface of target tissue. The tissue-engaging head may be malleable thereby allowing a surgeon to shape the head to conform to the surface of target tissue. The tissue-engaging head may be rigid having a shape conforming to the surface of target tissue. The tissue-engaging head may comprise a tissue contact surface. The tissue contact surface of the tissue-engaging head may be shaped or is shapeable to conform to the surface of the target tissue.

In one embodiment of the present invention, the tissue-engaging head of device 20 is formed of medical grade silicone rubber or thermoplastic elastomeric material (e.g., polyurethane). Preferably, the material selected in this embodiment has a low durometer (e.g., about 50) so that the tissue-engaging head may conform to the surface of the heart. The material selected may be a substantially transparent or translucent material. Further contemplated are embodiments in which the tissue-engaging head is made of multiple materials of different durometers and properties, to form, for example, an endoskeleton or exoskeleton to provide varying degrees of stiffness and flexibility along different portions of the tissue-engaging head.

The tissue-engaging head may comprise one or more suction or vacuum ports, openings, orifices, channels or elements positioned on, along, within or adjacent a tissue contact surface. The suction ports, openings, orifices, channels or elements may communicate suction through the tissue contact surface to the atmosphere. A tissue-engaging suction head is designed to engage or grasp tissue via suction. Each suction port, opening, orifice, channel or element may have a suction aperture coupling the port, opening, orifice, channel or element to a suction conduit, passageway or lumen. The suction aperture may be located in the center or at a position slightly off-center of the suction port, opening, orifice, channel or element. The suction aperture may be any shape including circular, oval, rectangular, or triangular. Each suction port, opening, orifice, channel or element may also be any suitable shape, for example circular, oval, rectangular, or triangular.

Preferably, each suction aperture would have a smaller diameter than the area of each suction port, opening, orifice, channel or element. A smaller diameter creates a high resistance pathway between the suction port, opening, orifice, channel or element and the suction conduit. Because of the high resistance pathway, loss of a tissue-to-port seal in one suction port (and thus loss of fixation of the suction port to the tissue) should not cause a precipitous pressure drop in the remainder of the suction ports.

Suction ports, openings, orifices, channels and/or elements may be arranged in any suitable fashion, such as a row or circle. In addition, the specific number of ports and their position may vary. Tissue-engaging head of device 20 may be covered with a removable covering during insertion into a patient's body to prevent blood or tissue from clogging the suction openings, although this is not necessary. Such coverings may include coverings of biocompatible material that would cover the entire tissue-engaging head of device 20. Alternatively, coverings may be placed just over the ports, such as, for example, mesh coverings or ribbed coverings.

A flexible tissue-engaging head may help to seal the head against tissue thereby helping to maintain suction. A sufficiently flexible head may draw down toward the surface of the heart more than the surface of the heart is pulled up into the tissue-engaging head.

In one embodiment of the present invention, the tissue-engaging head may comprise one or more mechanical means for engaging and/or grasping tissue. For example, the tissue-engaging head may comprise one or more hooks, clamps, screws, barbs, sutures, straps, tethers and/or staples. The tissue-engaging head may comprise a cuff or basket-type device designed to fit completely or partially around an organ, e.g., a heart. The tissue-engaging head may comprise one or more chemical means for engaging and/or grasping tissue. For example, the tissue-engaging head may comprise tissue glue or adhesive. The tissue-engaging head may comprise one or more coupling means for engaging and/or grasping tissue. For example, a suction means in addition to a mechanical means may be used to engage or grasp tissue. A magnetic means may also be used to engage or grasp tissue.

Figure 3:
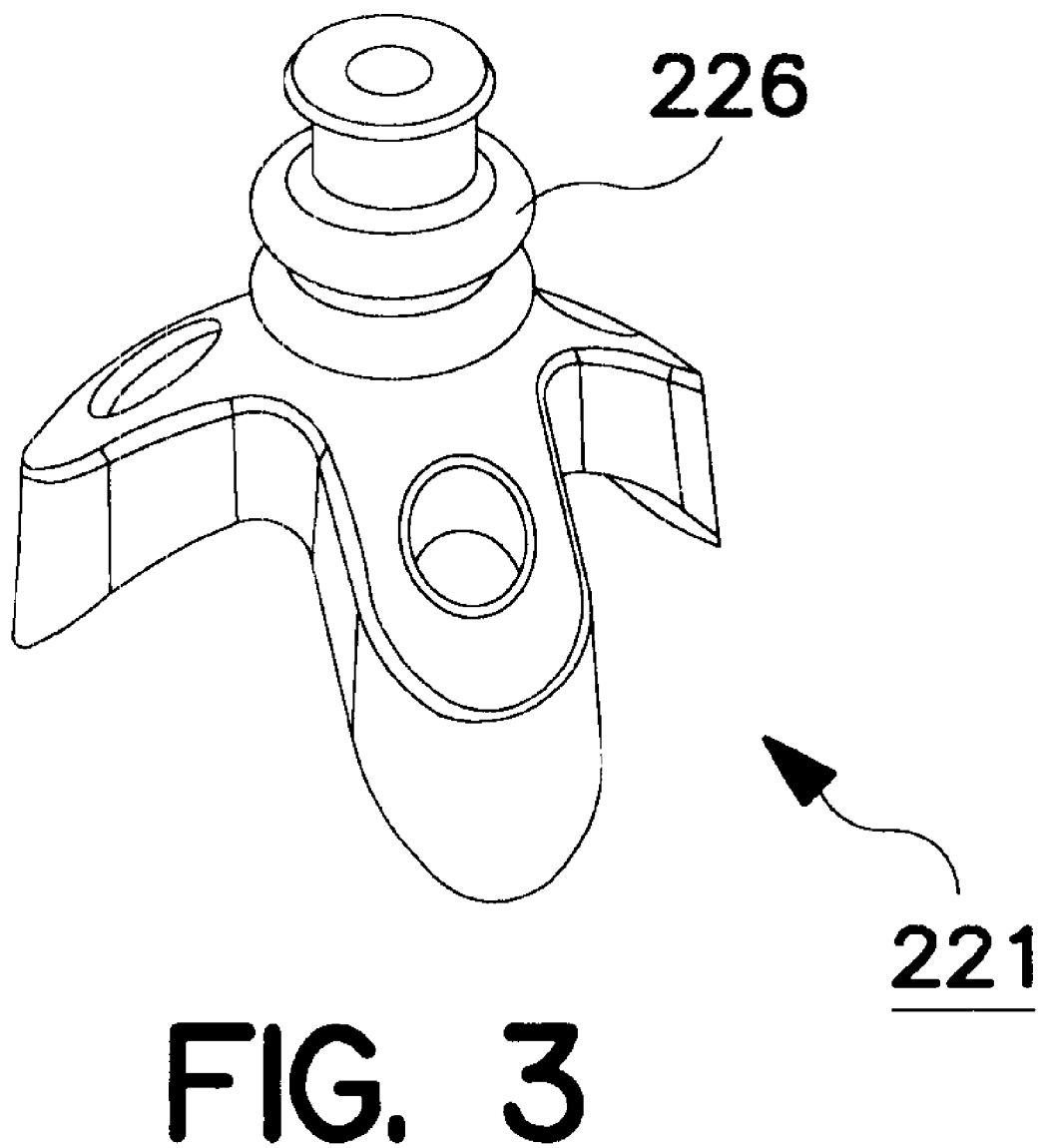
FIG. 3 is a top view of one embodiment of a tissue-engaging head of a medical device in accordance with the present invention.

In one embodiment of the present invention, the tissue-engaging head 221, as shown in FIG. 3, may comprise a plurality of legs that may flex to conform to the surface of the heart. The legs of the tissue-engaging head may be arranged in starfish-shaped configuration. Preferably in this embodiment, there are 2–4 legs and, most preferably, there are 3 legs. The legs may be generally arcuate, curving downwardly away from the attached ends of the legs to the free ends of the legs. The legs may be sufficiently flexible that they may bend to conform to flat or curved surfaces, facilitating use of the tissue-engaging head at the apex or elsewhere on the heart.

In use, the legs may allow the tissue-engaging head to be oriented to avoid placement over particular features of the heart anatomy, such as the cardiac arteries, or to avoid conflict with other surgical devices, such as a heart stabilizer of the type sold under the trade designation "OCTOPUS" by Medtronic, Inc., Minneapolis, Minn., USA.

In one embodiment of the present invention, the tissue-engaging head of device 20 may be sufficiently resiliently flexible that it may flex to allow it to be pushed through a small incision, cannula or port. Once inside the chest cavity, the flexible head will return to its original shape. For example, the legs may be configured and sufficiently flexible that they can be drawn against one another to a collapsed position for entering into a thoracic cavity through a small incision, cannula or port in endoscopic and/or closed chest surgery. In addition, to closed chest surgery, this invention is applicable to open chest/split sternum surgery, in particular open chest, beating heart surgery for repositioning the heart to improve access to various coronary arteries.

Figure 4:
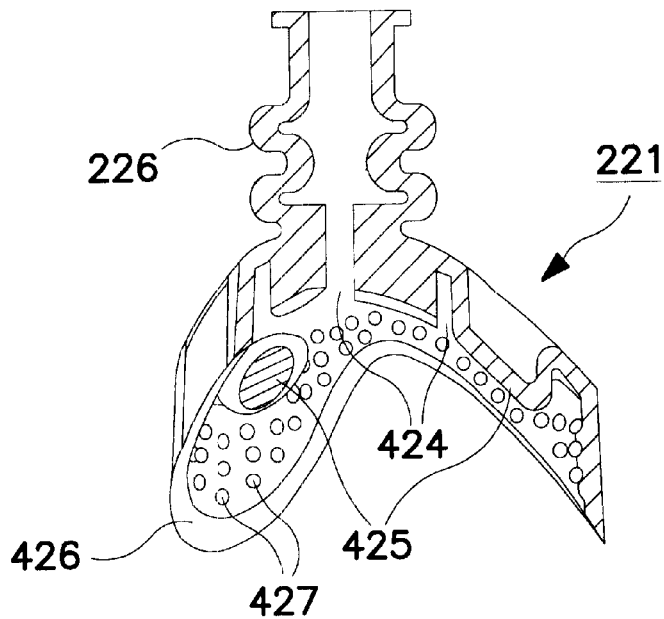
FIG. 4 is a cross-sectional view of one embodiment of a tissue-engaging head of a medical device in accordance with the present invention.
Figure 5:
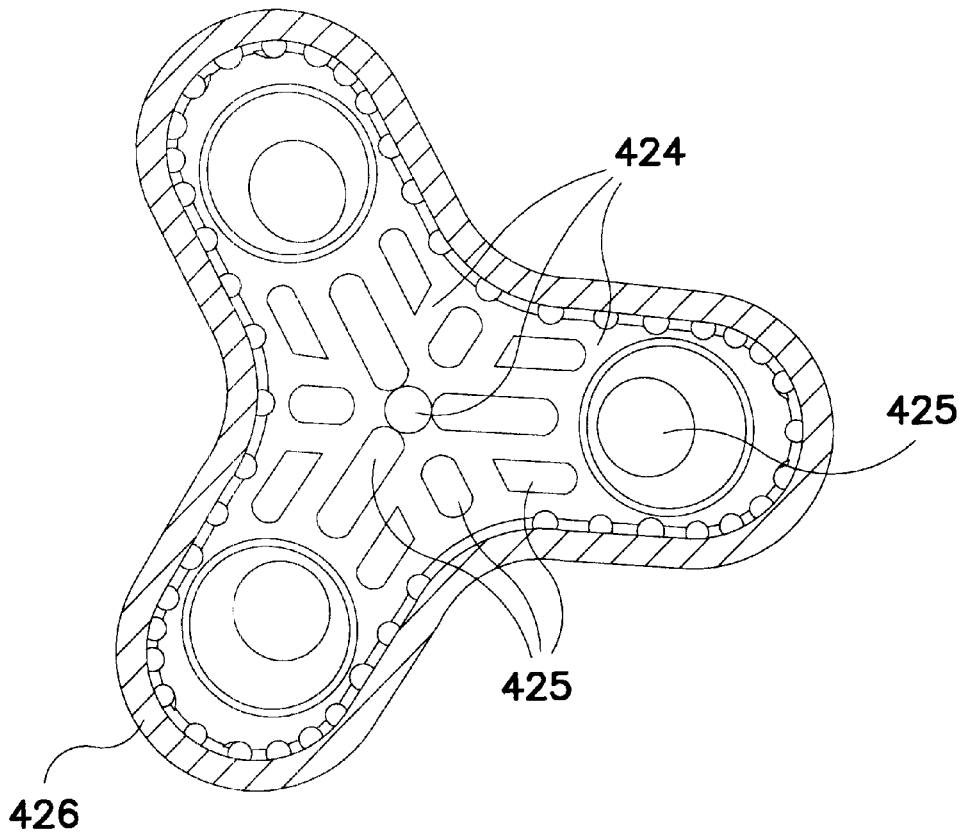
FIG. 5 is a bottom view of one embodiment of a tissue-engaging head of a medical device in accordance with the present invention.

One or more suction ports, openings, orifices, channels and/or elements 424 may be provided along a tissue contact surface or tissue-engaging face of suction head 221 in fluid communication with the legs to apply suction between the legs and the surface of the heart to grasp the surface (see FIGS. 4 and 5). One or more suction ports, openings, orifices, channels and/or elements may be positioned in or on each leg.

As shown in FIGS. 4 and 5, one or more tissue-engaging members or standoffs 425 may be provided within the tissue-engaging head to prevent vacuum channels from being closed off as tissue and the suction head are drawn together to allow continued fluid communication along the vacuum channels. In addition, one or more tissue-engaging members may be provided adjacent the orifice of a vacuum passageway to prevent the orifice and tissue being drawn together to close the orifice, thereby maintaining fluid communication between the vacuum passageway and the vacuum channels.

Figure 6:
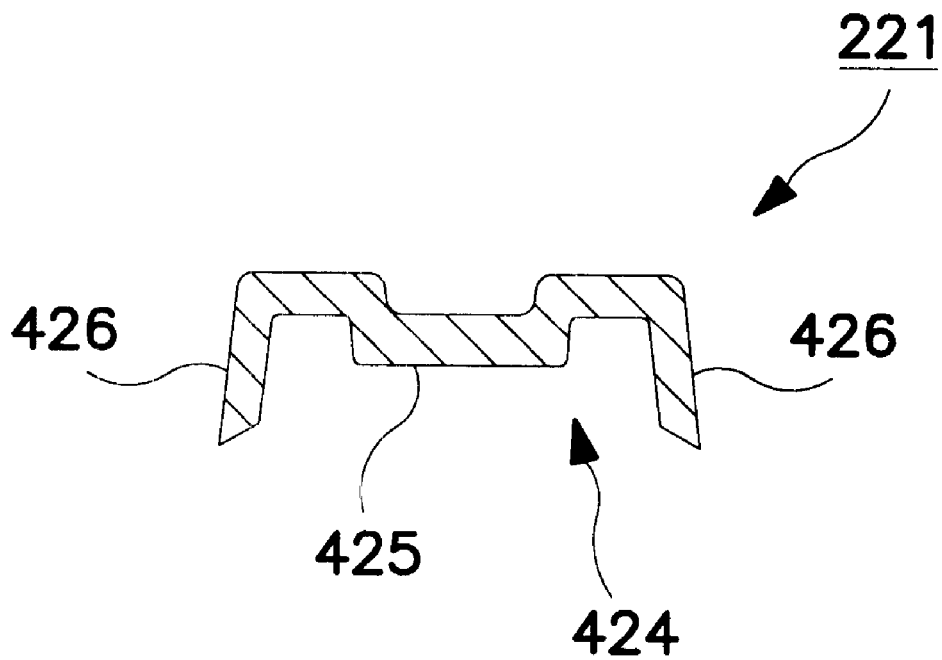
FIG. 6 is a cross-sectional view of one embodiment of a tissue-engaging head of a medical device in accordance with the present invention.
Figure 7:
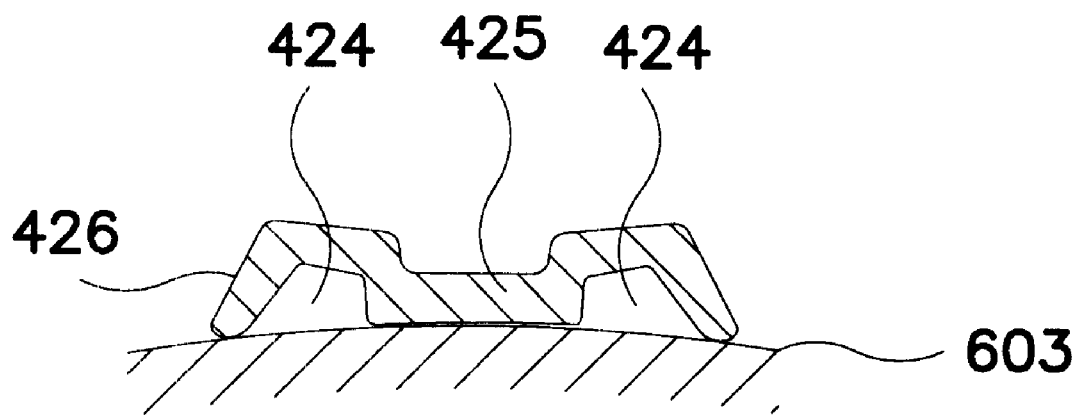
FIG. 7 is a cross-sectional view of one embodiment of a tissue-engaging head of a medical device in accordance with the present invention.

FIGS. 6 and 7 illustrate one embodiment of a tissue-engaging suction head 221 in which a resiliently flexible flange 426 (also shown in FIG. 4) resiliently deforms against heart tissue 603 to form a seal to help maintain the vacuum in vacuum channel 424. The standoff or tissue-engaging member 425 limits how far suction head 221 may be pulled down toward the surface of the heart to maintain vacuum channel 424, as illustrated in FIG. 7. Tissue-engaging members may be elongated having a direction of elongation extending generally radially with respect to an orifice.

The end of each flange may be beveled as illustrated in FIG. 4 so that the laterally outward edge of each end extends further than the laterally inward edge of each end. Flange 426 may extend along substantially the entire periphery of suction head 221, see FIG. 5, so that vacuum can be maintained in the area defined between flange 426, the body of suction head 221 and the surface of the heart.

Tissue-engaging head of device 20, may comprise one or more bumps 427, for example, located on the inner surface of resiliently flexible peripheral flange 426, see FIG. 4. Most preferably, bumps 427 are generally hemispherical convex structures forming an integral part of the inner surface of the peripheral flange 426. When suction is pulled through vacuum channel 424, bumps 427 are pulled against the surface of an organ as flange 426 deforms against the surface of the organ, e.g., the epicardium of the heart. Bumps 427 help retain suction head 221 in place on the heart. Bumps 427 may be arranged in an alternating pattern, aligned pattern or irregular pattern, for example.

Textures other than bumps are also contemplated, such as dimples, spikes, ridges, grooves (e.g., microgrooves), roughened texture (e.g., microtextured), surface grain, strips, ribs, channels, ruts, embedding or adhering abrasive particles in or on the surface, gluing or laminating the texture onto the surface, or other surface treatments, conditions or configurations that increase the grip of the inner surface of the tissue-engaging head on the epicardium. It is also contemplated that the other underside surfaces of the tissue-engaging head may be textured to increase surface area and/or gripping. For example, a texture is preferably provided on the tissue-engaging members or standoffs 425, and this texture may be in the same form as the texture on the inner surface of the peripheral flange 426 or a different gripping texture. The texture may be formed by any suitable methods, such as by molding, chemical etching, roughening with sandpaper or other abrasives (e.g., sand blasting), electrical means (such as EDM machining), thermal means, or laser etching, for example.

FIG. 2 illustrates one embodiment of the tissue-engaging head 221 in which tube fitting 224 includes a ninety degree bend. Other tube fittings having other angles of bend are also contemplated. The tube fitting 224 receives a vacuum line (not shown in FIG. 2). Tissue-engaging head 221 and tube fitting 224 may be free to rotate relative to the end of support arm 222. FIG. 2 also illustrates yet one embodiment of tissue-engaging head 221 in which a filter element 225 is provided within the tube fitting 224. The filter element 225 preferably includes a through bore.

Figure 8:
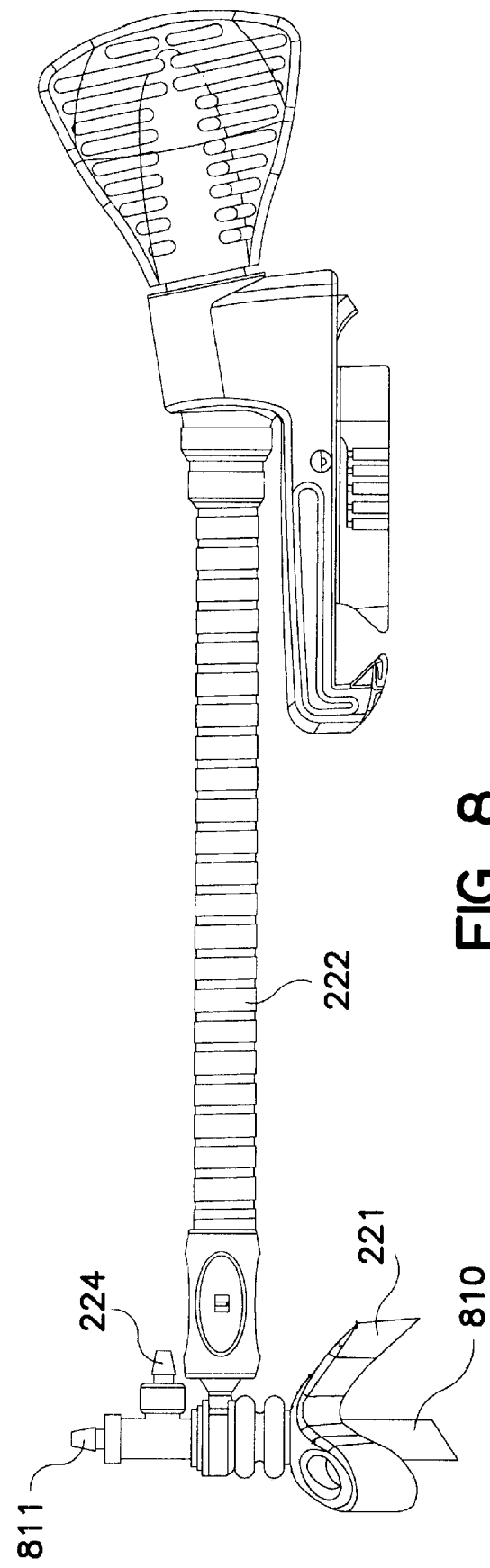
FIG. 8 is a side view of one embodiment of a medical device in accordance with the present invention.
Figure 9:
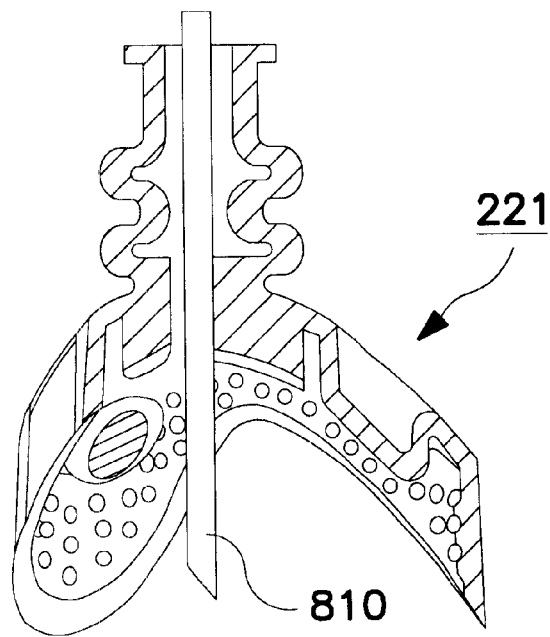
FIG. 9 is a cross-sectional view of one embodiment of a tissue-engaging head of a medical device in accordance with the present invention.
Figure 10:
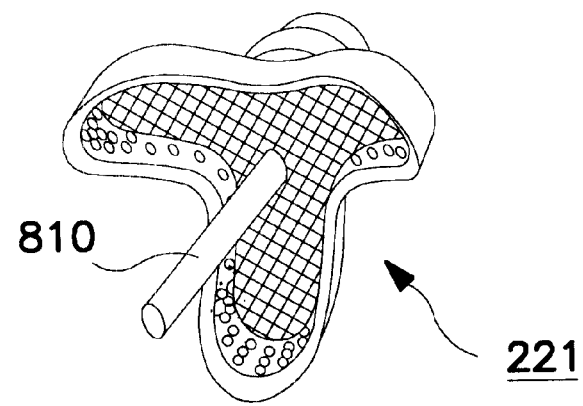
FIG. 10 is a bottom view of one embodiment of a tissue-engaging head of a medical device in accordance with the present invention.

The tissue-engaging device 20 may include one or more fluid openings for delivery and/or removal of one or more fluids. Tissue-engaging device 20 may include needles for injection of fluids, drugs and/or cells into organ tissue. As shown in FIGS. 8, 9 and 10, tissue-engaging device 20 may comprise catheter or cannula 810 for blood removal or delivery into an organ, e.g., a heart. In the case of the heart, the cannula or catheter may be placed through the wall of the heart and into an interior chamber of the heart comprising blood, for example, into the left ventricle. Blood may be removed or delivered via a blood pump. For example, tube fitting 811, which is in fluid communication with catheter or cannula 810, may be attached to a CPB circuit or a cardiac assist circuit such as an LVAD circuit. Tissue-engaging device 20 may include one or more openings for delivery or removal of one or more gases including smoke evacuation.

As mentioned earlier and as shown in FIG. 11, one or more tissue-engaging members or standoffs 425 may be provided within the tissue-engaging head to prevent vacuum channels from being closed off as tissue and the suction head are drawn together to allow continued fluid communication along the vacuum channels. Alternatively or in addition to standoffs, a porous screen, mesh and/or fabric 450 (as shown in FIG. 12) may be used to prevent the orifice and tissue being drawn together to close the orifice, thereby maintaining fluid communication between the vacuum passageway and the vacuum channels. The screen, mesh and/or fabric may engage or contact tissue. The screen, mesh and/or fabric may be placed on top of standoffs. The screen, mesh and/or fabric may comprise a number of materials including metallic, ceramic and/or polymeric materials. The screen, mesh and/or fabric may be made of a synthetic or natural material. In one embodiment of the present invention, the mesh may be made of a medical grade Dacron material. As shown in FIG. 13, the screen, mesh and/or fabric may comprise bumps 451. Alternatively or in addition to standoffs, a porous foam 452 (as shown in FIG. 14), e.g., a polymeric foam, or other porous material or materials may be used to prevent the orifice and tissue being drawn together to close the orifice, thereby maintaining fluid communication between the vacuum passageway and the vacuum channels.

The tissue-engaging head may be designed to be an implantable medical device. For example, following a medical procedure such as a CABG procedure the tissue-engaging head may be left within the patient, thereby providing benefit to the patient. The tissue-engaging head may be made of one or more biodegradable materials, thereby allowing the head to be absorbed by the patient over time.

Tissue-engaging device 20 may comprise a maneuvering or support apparatus or means such as a shaft, a handle or an arm 222, as shown in FIGS. 2 and 8, connected to the tissue-engaging head to position the head to thereby position or hold tissue such as the heart. The support shaft, handle or arm may be rigid, flexible, telescoping or articulating. The shaft, handle or arm may comprise one or more hinges or joints for maneuvering and placing device 20 against tissue. The hinges or joints of the maneuvering or support apparatus may be actuated remotely, for example with pull wires, from outside a patient's body. The shaft, handle or arm may be malleable or shapeable. The maneuvering or support means may be made of a shape memory alloy wherein heat may be use to change the shape of the maneuvering or supporting means.

The support shaft, handle or arm may be of the type that can readily be changed between a flexible or articulating condition and a rigid condition. For example, a support arm may comprise a plurality of rigid members that are free to articulate relative to one another until a central cable pulls the rigid members together to lock the support arm in a rigid condition. The cable is controlled, for example, by a handle that rotates to pull tension on the cable, thereby drawing the rigid members together to lock them into position. Each rigid member has opposite ends, one of which is concave and the other of which is convex (e.g., hemispherical). The convex end of one rigid member fits into the concave end of the adjacent rigid member, and allows the member to articulate relative to the adjacent member if the central cable has not been tensioned to lock the rigid members together. Most preferably, the rigid members are not of uniform cross section, with the rigid members closer to the distal end having a smaller cross section than the rigid members closer to the proximal end. A suitable articulating mechanism could be similar to the type used in the "OCTOPUS 3"™ tissue stabilization system sold by Medtronic, Inc., Minneapolis, Minn. USA. See, also, the articulating arm mechanisms disclosed in U.S. Pat. Nos. 5,836,311; 5,927,284 and 6,015, 378, co-assigned U.S. patent application Ser. No. 09/396,047, filed Sep. 15, 1999; and Ser. No. 09/678,203, filed Oct. 2, 2000, and European Patent Publication No. EP 0 993 806.

The tissue-engaging head of suction device 20 may be rigidly, permanently, moveably, or removeably coupled, connected or mounted onto the maneuvering or support apparatus or means. For example, the head may be coupled via a hinge or joint to an articulating support arm. The head may be coupled, for example, to the maneuvering or support apparatus via one or more springs, hinges, joints and/or bellows. The tissue-engaging head may be designed to be detachable or replaceable; for example, the head may snap on and/or off the maneuvering or support apparatus. Magnets, glues, screws and/or bolts may also be used to attach the tissue-engaging head to the maneuvering or support apparatus. Also contemplated is use of sets of tissue-engaging heads of different sizes and/or shapes.

The mechanism connecting the tissue-engaging head to the support arm may permit the head to rotate and/or pivot on one or more axes relative to the support arm. For example, the tissue-engaging head may be permitted to rotate relative to the support arm along a first axis, and the tissue-engaging head may be allowed to pivot relative to the support arm along a second axis generally perpendicular to the first axis. The tissue-engaging head may be allowed to pivot and/or rotate along one or more axes even after the support arm is locked into a rigid condition.

The mechanism connecting the tissue-engaging head to the support arm may comprise one or more resiliently-flexible suspension elements. The tissue-engaging head and suspension element may be integrally molded of the same material. As used herein, "integral" or "integrally molded" refer to constructions in which one continuous piece is formed, rather than separate pieces that are connected together (e.g., mechanically or by welding or adhesive). The suspension element may comprise a bellows type structure that resiliently flexes to allow the tissue-engaging head to move in response to beating of the heart. The suspension element may be expandable to allow the tissue-engaging head to stretch or move toward and away from the support arm in response to the beating heart. The suspension element may allow movement including rotational and twisting motions in one or more directions.

In one embodiment of the present invention, the suspension element comprises a bellows 226 (as shown in FIGS. 2 and 3) that flexes as the suspension element is stretched. As the bellows is stretched, the effective spring rate of the suspension element increases. A suction and/or fluid passageway, conduit or lumen may extend through the bellows-type suspension element 226 (as shown in FIG. 4). The bellows may provide the further advantage of keeping the one or more passageways, conduits or lumens open through normal stretching of the bellows. In an alternate embodiment, the suspension element comprises a two-stage or multi-stage bellows providing a varying spring rate between stages, as well as a high spring rate when the bellows is stretched out.

Figure 15:
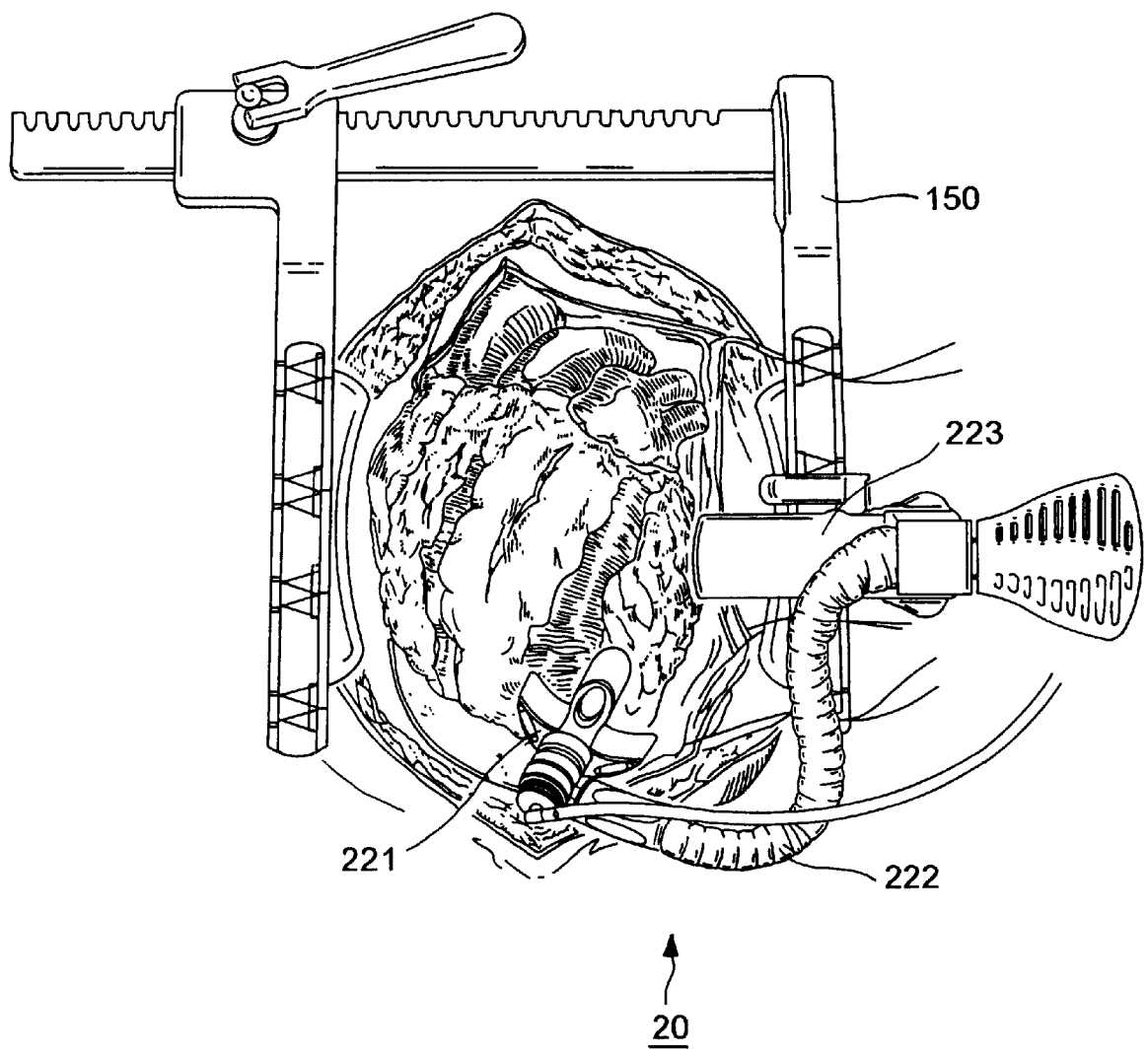
FIG. 15 is an illustration of one embodiment of a medical device in use in accordance with the present invention.
Figure 16:
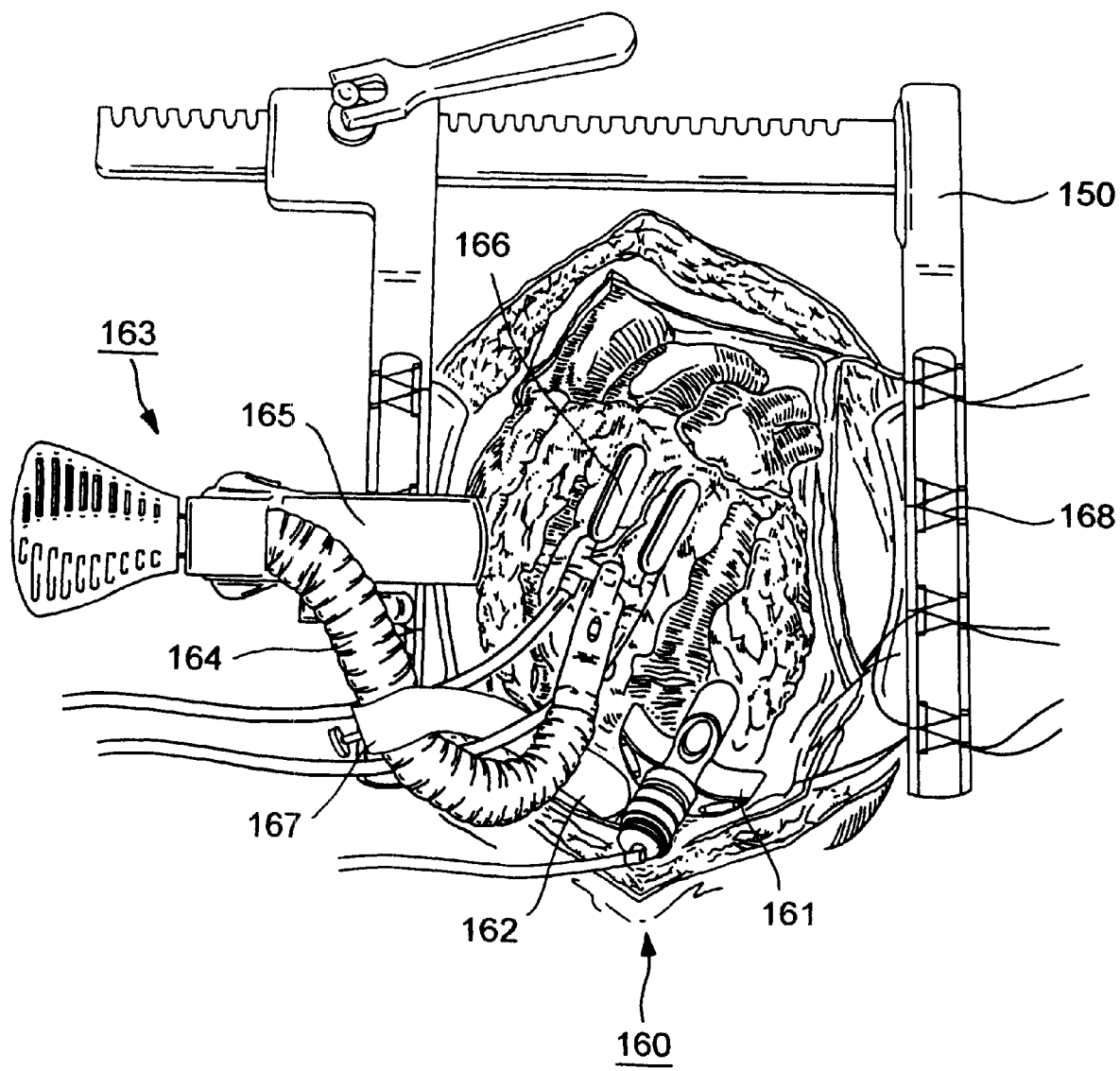
FIG. 16 is an illustration of one embodiment of a medical device in use in accordance with the present invention.

Tissue-engaging device 20 may be fixed in position relative to a patient. For example, the maneuvering or support apparatus of device 20 may be designed to attach to or lock onto one or more stable objects such as an operating table, a retractor, an endoscopic port and/or a support arm of another tissue-engaging apparatus. A retractor may be, for example, a sternal retractor or a rib retractor. An endoscopic port may be, for example, a cannula, such as a trocar cannula placed in a patient's chest. A portion of a patient's skeletal system may also be considered a stable object. FIG. 15 shows tissue-engaging device 20 locked onto a sternal retractor 150 fixed to a patient's chest. In FIG. 15, tissue-engaging device 20 is shown supporting a patient's heart while it is engaged or attached to the apex of the patient's heart. The patient's heart may be beating or stopped. FIG. 16 shows another embodiment of the present invention wherein support arm 162 of a first tissue-engaging device 160 is attached or coupled via clamp 167 to support arm 164 of a second tissue-engaging device 163. Clamp 167 may be designed to couple or attach onto a variety of stable objects including the support arms of various tissue-engaging devices. The second tissue-engaging device 163 is shown in FIG. 16 clamped onto a retractor 150 that is fixed to a patient's chest via clamp 165. Retractor 150 is shown in FIG. 16 to comprise suture holders 168. In FIG. 16, the first tissue-engaging device 160 is shown supporting a patient's heart while head 161 of device 160 is engaged or attached to the apex of the heart; the second tissue-engaging device 163 is shown stabilizing or immobilizing an area of the heart while head 166 of device 163 is engaged or attached to the surface of the heart. In this embodiment of the present invention, the patient's heart may be beating or stopped.

The maneuvering or support apparatus may comprise one or more lumens or conduits for communicating suction and/or delivering and/or removing fluids and/or gases to the tissue-engaging head. The one or more conduits or lumens may be connected to at least one suction opening and/or fluid opening located on tissue-engaging device 20.

Figure 17:
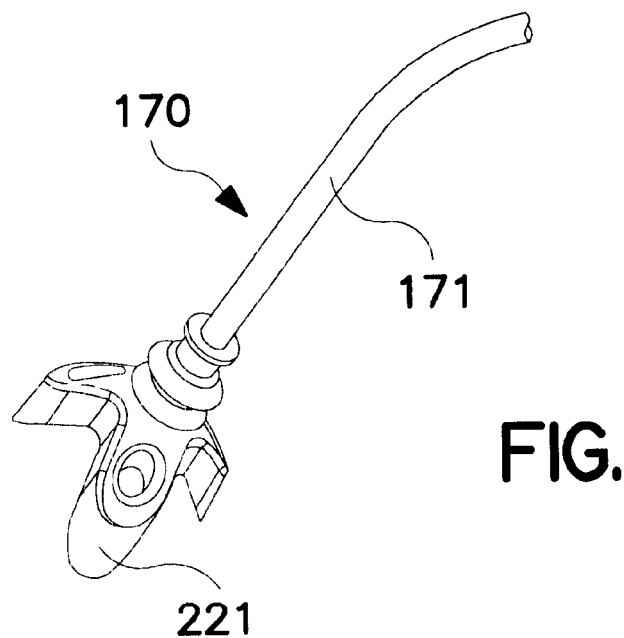
FIG. 17 is an illustration of one embodiment of a medical device in use in accordance with the present invention.
Figure 18:
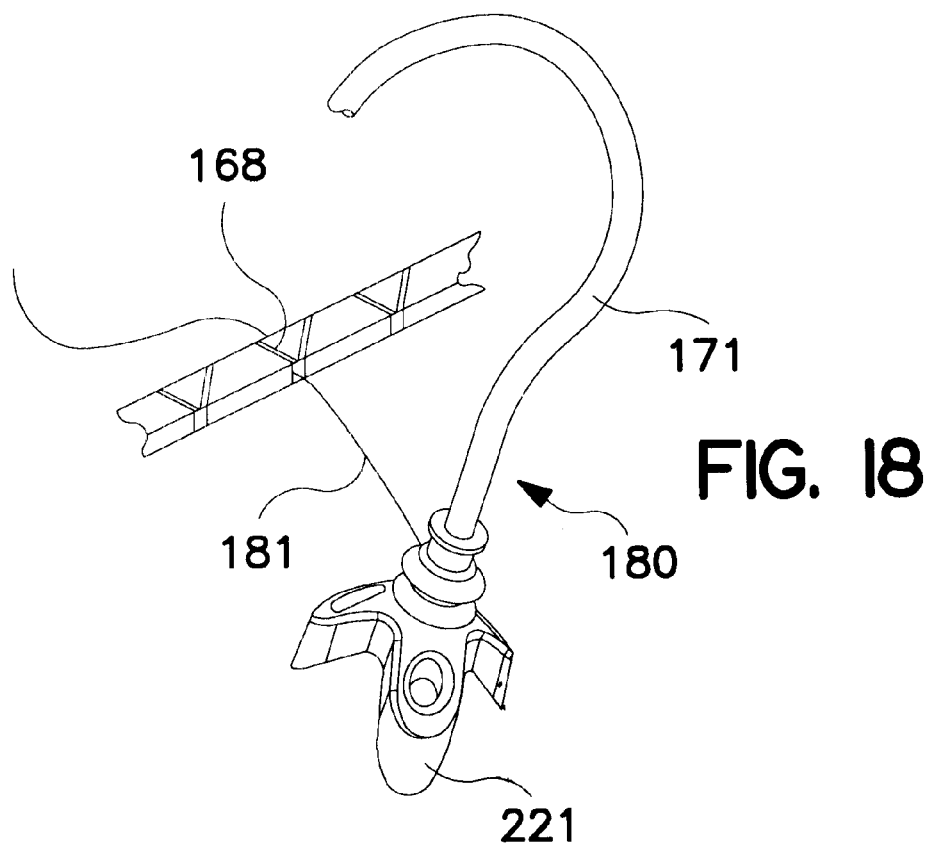
FIG. 18 is an illustration of one embodiment of a medical device in use in accordance with the present invention.

In one embodiment of the present invention, the maneuvering or support apparatus may be a suture, strap or tether. For example, the tissue-engaging head of device 20 may be attached to one or more sutures, straps or tethers which may be affixed or attached to a stable object such as a retractor. For example, FIG. 17 illustrates a tissue-engaging device 170 comprising a suction head 221 and a vacuum tube 171, which provides vacuum to suction head 221 and provides a tether or means for manipulating and holding suction head 221 to position and orient the heart. FIG. 18 illustrates a tissue-engaging device 180 comprising a suction head 221, vacuum tube 171, and suture, line or strap 181 that provides a tether or means for manipulating and holding suction head 221 to position and orient the heart. The suture, line or strap may be retained in a suture guide, clamp or lock 168, for example, on a sternal retractor (as shown in FIG. 16), although it is also contemplated that it could be retained on a rib retractor, port, cannula or other device or mechanism, or mounted on the patient, operating table or other stable or stationary object.

The tissue-engaging head may comprise one or more energy transfer elements positioned on, along, within or adjacent a tissue contact surface. Energy transfer elements transfer energy to target tissue. For example, energy transfer elements may be conductive elements that may supply RF energy, microwave energy or ultrasound energy to target tissue. Energy transfer elements may be, for example, laser elements for supplying laser light to target tissue or they may be cryo elements. Two or more energy transfer elements or conductive elements of tissue-engaging device 20 may be arranged in a biopolar arrangement wherein at least one element is used as a positive electrode and at least one element is used as a negative electrode. One or more energy transfer elements or conductive elements of tissue-engaging device 20 may be arranged in a monopolar arrangement wherein at least one element is used as one electrode and an indifferent electrode is placed elsewhere on the patient's body such as the back, thigh or shoulder or another site other than the tissue-engaging device 20 site.

Figure 19:
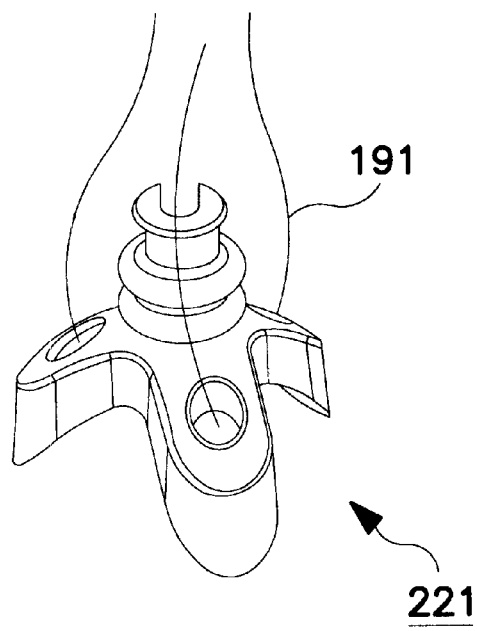
FIG. 19 is a side view of one embodiment of a tissue-engaging head of a medical device in accordance with the present invention.
Figure 20:
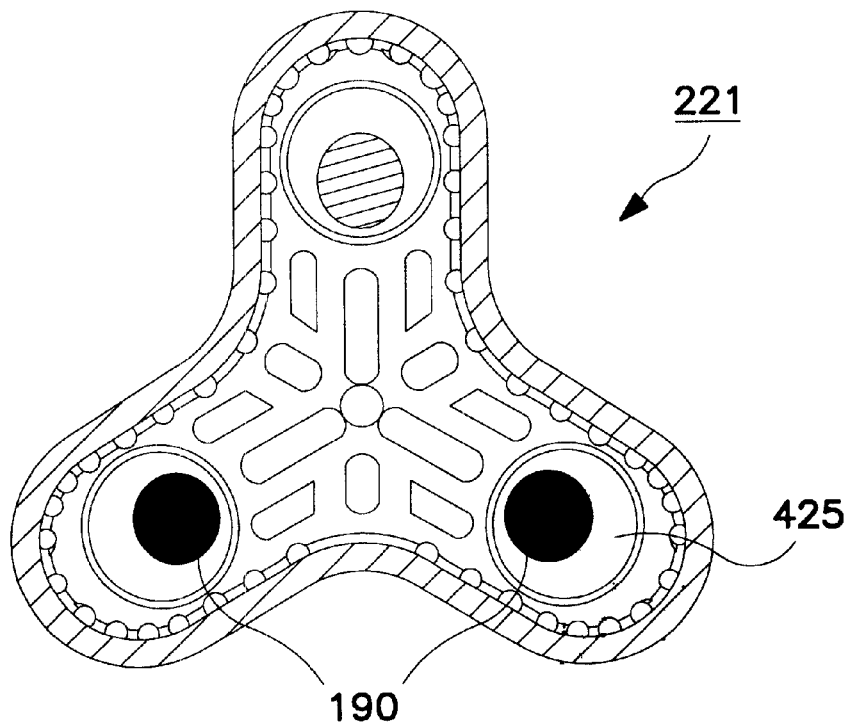
FIG. 20 is a bottom view of one embodiment of a tissue-engaging head of a medical device in accordance with the present invention.
Figure 21:
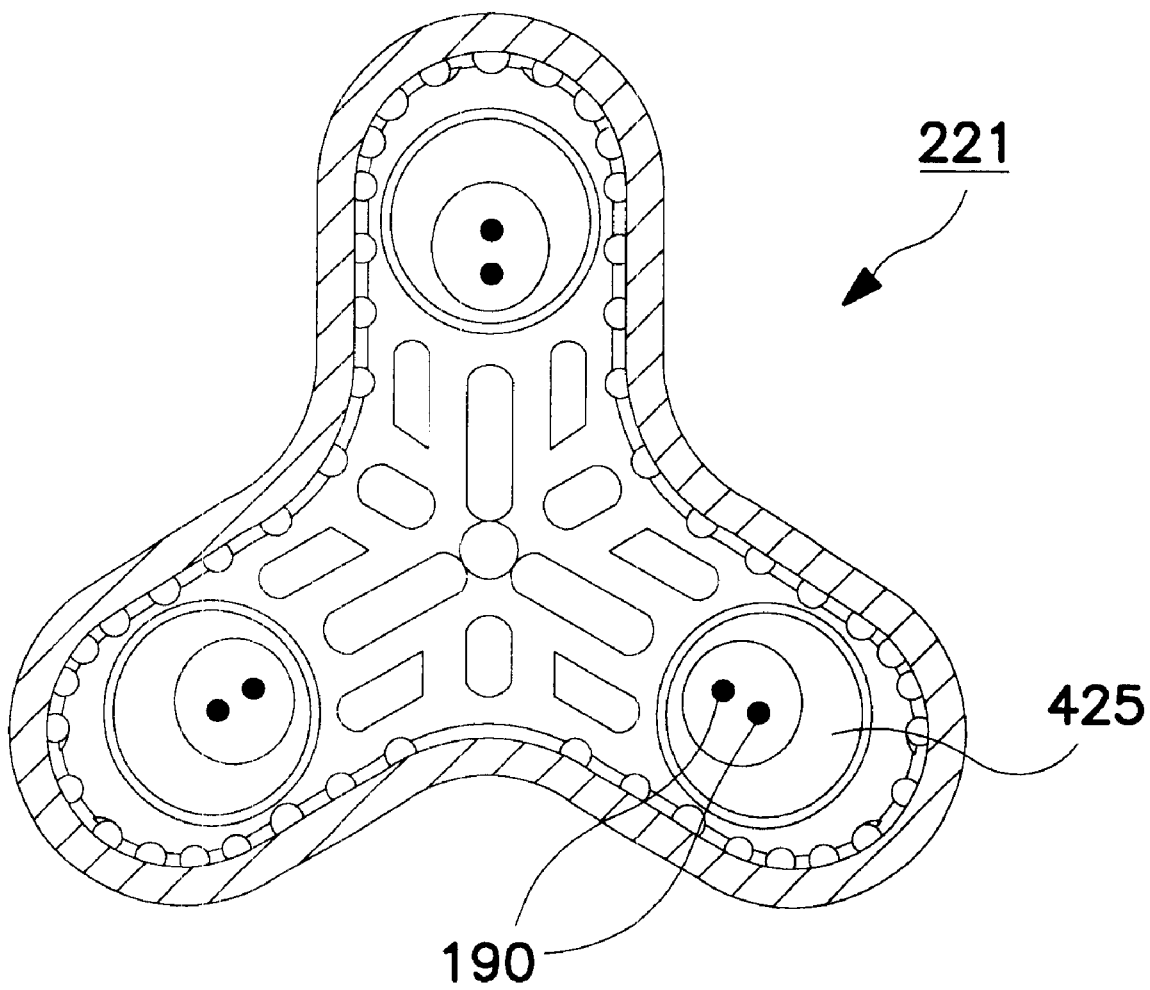
FIG. 21 is a bottom view of one embodiment of a tissue-engaging head of a medical device in accordance with the present invention.
Figure 22:
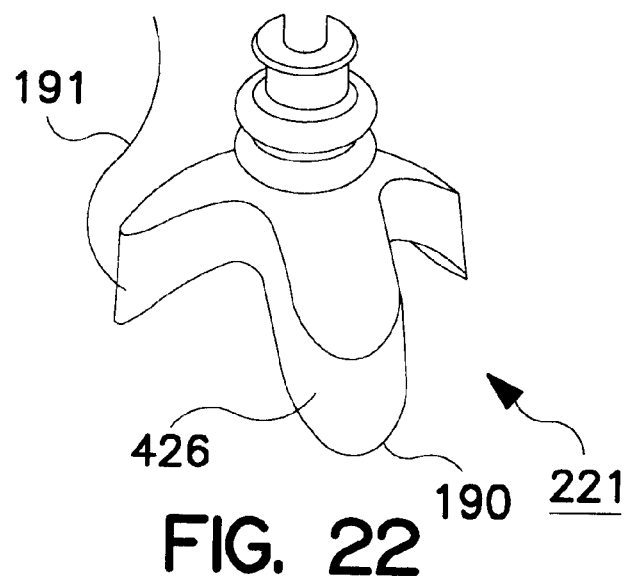
FIG. 22 is a side view of one embodiment of a tissue-engaging head of a medical device in accordance with the present invention.
Figure 23:
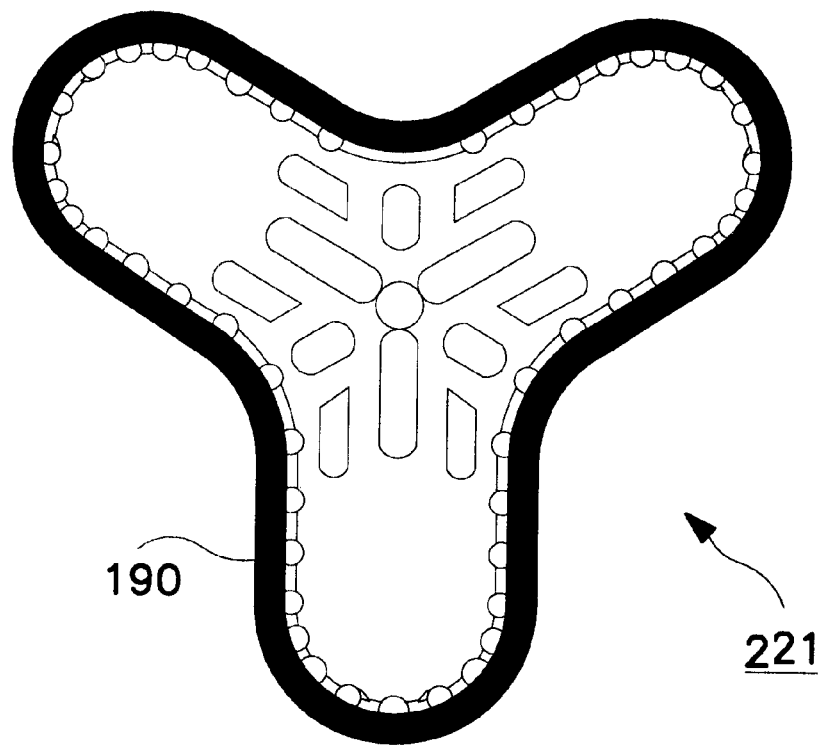
FIG. 23 is a bottom view of one embodiment of a tissue-engaging head of a medical device in accordance with the present invention.
Figure 24:
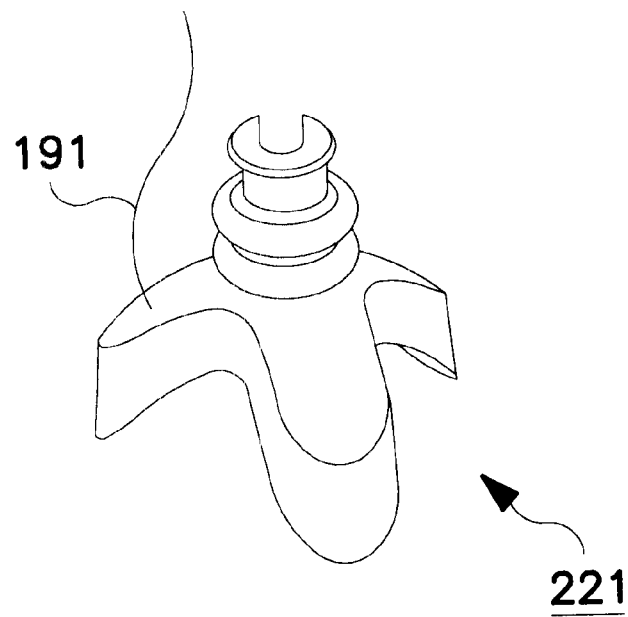
FIG. 24 is a side view of one embodiment of a tissue-engaging head of a medical device in accordance with the present invention.
Figure 25:
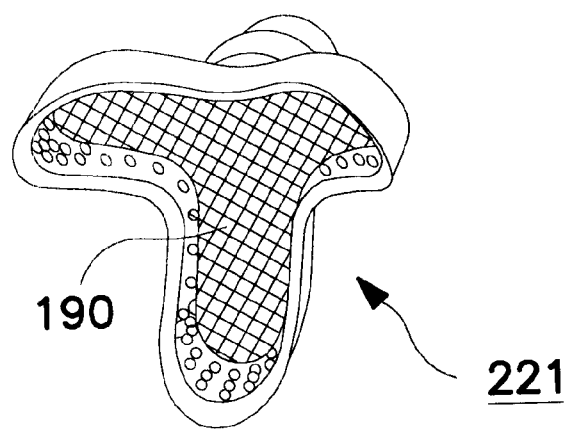
FIG. 25 is a bottom view of one embodiment of a tissue-engaging head of a medical device in accordance with the present invention.

As shown in FIGS. 19 and 20, tissue-engaging head 221 may comprise one or more energy transfer elements or electrodes 190. Electrodes 190 may be connected to energy source 50 (not shown in FIGS. 19 and 20) via electrically conductive wires or leads 191. One or more electrodes 190 may be positioned on one or more standoffs 425. For example, FIG. 20 shows two electrodes 190 each positioned on a different standoff 425. FIG. 21 shows six electrodes 190 positioned in pairs on three different standoffs 425. In another embodiment of the present invention, tissue-engaging head 221 may comprise lead 191 coupled to a perimeter electrode 190 positioned on or along flange 426 as demonstrated in FIGS. 22 and 23. In another embodiment of the present invention, tissue-engaging head 221 may comprise lead 191 coupled to a conductive screen or mesh electrode 190 as shown in FIGS. 24 and 25. For example, the conductive screen or mesh may be made of a metallic material or a conductive polymeric material or combinations thereof. In addition, electrode 190 may or may not be positioned on standoffs.

Energy transfer elements or conductive elements may comprise one or more conductive materials or blends including titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, conductive metals, conductive polymers or plastics, and/or conductive ceramics. Energy transfer elements or conductive elements may not be conductive but may serve as a conduit to deliver a conductive material such as a conductive fluid. Energy transfer elements or conductive elements may be porous. For example, energy transfer elements or conductive elements may comprise porous polymers, metals, or ceramics. Energy transfer elements or conductive elements may be coated with non-stick coatings such as PTFE or other types of coatings as discussed herein. Energy transfer elements or conductive elements may be flexible thereby allowing them to conform to the surface of target tissue. Energy transfer elements or conductive elements may be malleable thereby allowing a surgeon to shape them to conform to the surface of target tissue.

Energy transfer elements or conductive elements may comprise one or more metal conductors such as windings inside a polymer or a conductive mesh material. The energy transfer elements or conductive elements may comprise tubes for delivering fluids. The tubes may comprise holes or slots. A polymer tube may be placed inside a metal tube to control fluid deliver through energy transfer elements or conductive elements. One or more of the energy transfer elements or conductive elements may be used as one or more nerve stimulation electrodes and/or as one or more cardiac stimulation electrodes. Electrodes may be used for cardiac pacing, defibrillation, cardioversion, sensing, stimulation, and/or mapping.

Energy transfer elements or conductive elements may comprise needles designed to penetrate tissues such as fat and muscle. For example, energy transfer elements or conductive elements may be designed to penetrate fat on the heart thereby allowing the energy transfer elements or conductive elements to reach cardiac tissue. The needles may allow fluids such as conductive fluids, chemicals such as tissue ablation chemicals, drugs, biological agents and/or cells to pass through. The needles may allow a vacuum or suction to pass through.

Tissue-engaging device 20 may comprise one or more switches, e.g., a surgeon-controlled switch. One or more switches may be incorporated in or on tissue-engaging device 20 or any other location easily and quickly accessed by the surgeon for regulation of tissue-engaging device 20 by the surgeon. A switch may be, for example, a hand switch, a foot switch, or a voice-activated switch comprising voice-recognition technologies. A switch may be physically wired to device 20 or it may be a remote control switch.

Tissue-engaging device 20 may be slaved to suction source 30, fluid source 40, energy source 50, sensor 60 and/or processor 70. For example, tissue-engaging device 20 may be designed to automatically stop engaging tissue when processor 70 sends a signal to stop tissue engagement. Tissue-engaging device 20 may include a visual and/or audible signal used to alert a surgeon to any change in tissue engagement and/or a visual and/or audible signal may be included in system 10. For example, a beeping tone or flashing light may be used to alert the surgeon when tissue-engaging device 20 has engaged tissue. Tissue-engaging device 20 may be slaved to a robotic system or a robotic system may be slaved to tissue-engaging device 20.

Tissue-engaging device 20 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. Tissue-engaging device 20 may be guided into a desired position using various guidance techniques, e.g., flouroscopic guidance techniques.

Figure 26:
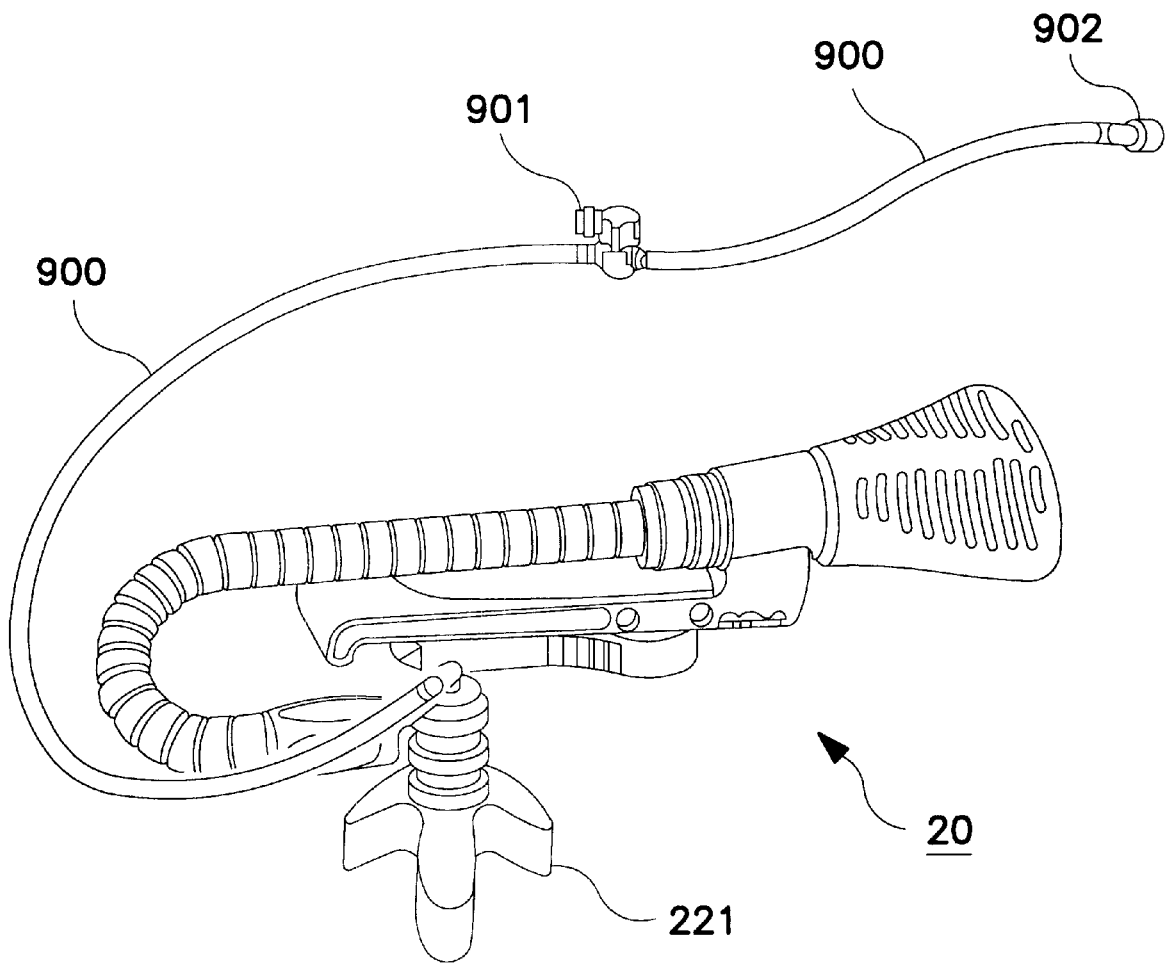
FIG. 26 is an illustration of one embodiment of a medical device in use in accordance with the present invention.
Figure 27:
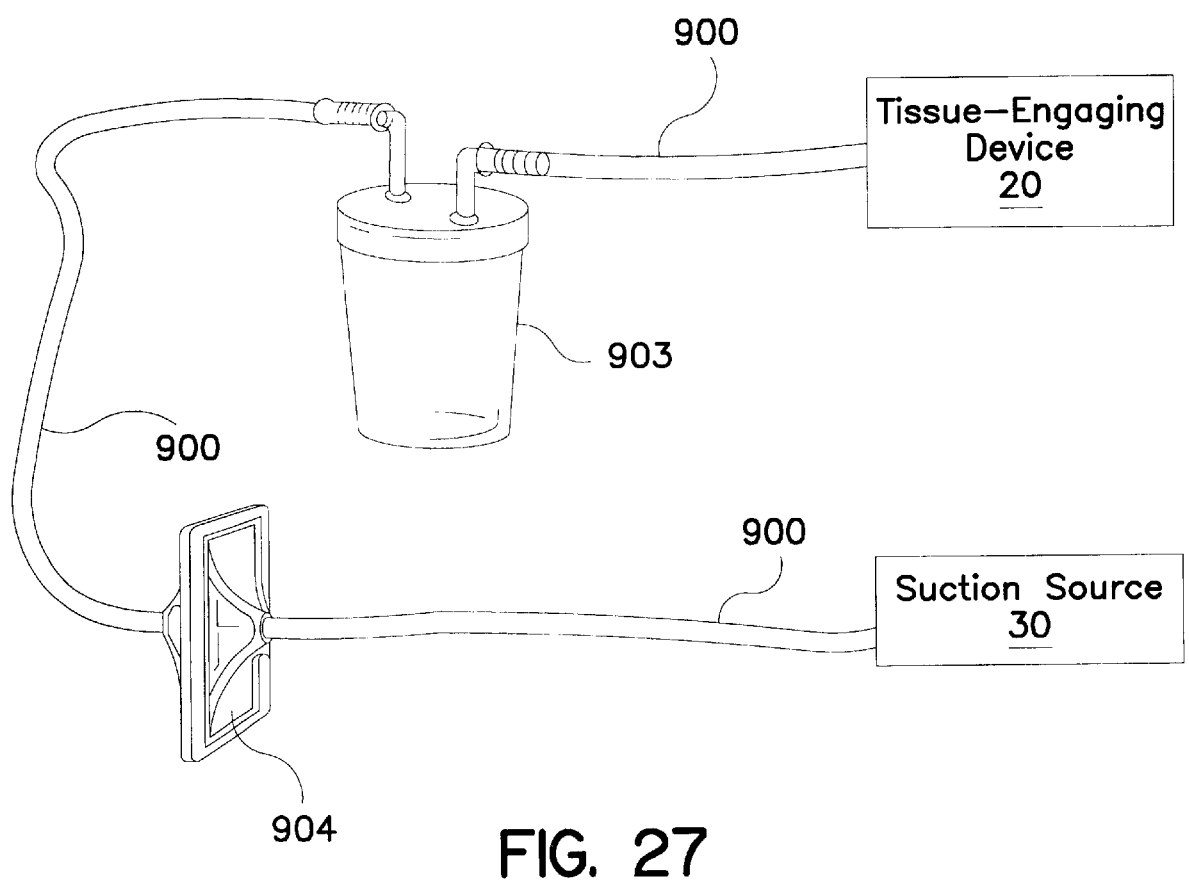
FIG. 27 is an illustration of one embodiment of a medical device in use in accordance with the present invention.

System 10 may include suction source 30 for providing suction to tissue-engaging device 20. As shown in FIG. 26, tissue-engaging device 20 may be attached to a flexible or rigid hose or tubing 900 for supplying suction and/or fluids from a suitable suction source and/or fluid source to the target tissue surface through suction and/or fluid elements, openings, orifices, or ports of device 20. Tubing 900 may comprise one or more stopcocks 901 and/or connectors 902 such as luer connectors. Suction may be provided to device 20 by the standard suction available in the operating room. Suction source 30 may be coupled to tissue-engaging device 20 with a buffer flask 903 and/or filter 904 as shown in FIG. 27. Suction may be provided at a negative pressure of between 200–600 mm Hg with 400 mm Hg preferred. As used herein, the terms "vacuum" or "suction" refer to negative pressure relative to atmospheric or environmental air pressure in the operating room.

Alternatively, suction may be provided via one or more manual or electric pumps, syringes, suction or squeeze bulbs or other suction or vacuum producing means, devices or systems. Suction source 30 and/or tubing 900 may comprise one or more vacuum regulators, resistors, stopcocks, connectors, valves, e.g., vacuum releasing valves, filters, conduits, lines, tubes and/or hoses. The conduits, lines, tubes, or hoses may be flexible or rigid. For example, a flexible suction line may be used to communicate suction to device 20, thereby allowing device 20 to be easily manipulated by a surgeon. Another method that would allow the surgeon to easily manipulate device 20 includes incorporation of suction source 30 into device 20. For example, a small battery operated vacuum pump or squeeze bulb may be incorporated into device 20.

Suction source 30 may be slaved to tissue-engaging device 20, fluid source 40, energy source 50, sensor 60 and/or processor 70. For example, suction source 30 may be designed to automatically stop suction when processor 70 sends a signal to stop suction. Suction source 30 may include a visual and/or audible signal used to alert a surgeon to any change in suction. For example, a beeping tone or flashing light may be used to alert the surgeon when suction is present. Suction source 30 may be slaved to a robotic system or a robotic system may be slaved to suction source 30. Suction may be used to secure, anchor or fix tissue-engaging device 20 to an area of tissue. The area of tissue may comprise a beating heart or a stopped heart. Suction may be used to remove or aspirate fluids from the target tissue site. Fluids removed may include, for example, blood, saline, Ringer's solution, ionic fluids, contrast fluids, irrigating fluids and energy-conducting fluids. Steam, vapor, smoke, gases and chemicals may also be removed via suction.

System 10 may include fluid source 40 for providing fluids to tissue-engaging device 20. Tissue-engaging device 20 may be attached to a flexible or rigid hose or tubing for supplying fluids from fluid source 40 to the target tissue through fluid elements, openings, orifices, or ports of device 20. Fluid source 40 may be any suitable source of fluid. Fluid source 40 may include a manual or electric pump, an infusion pump, a peristaltic pump, a roller pump, a centrifugal pump, a syringe pump, a syringe, or squeeze bulb or other fluid moving means, device or system. For example, a pump may be connected to a shared power source or it may have its own source of power. Fluid source 40 may be powered by AC current, DC current, or it may be battery powered either by a disposable or re-chargeable battery. Fluid source 40 may comprise one or more fluid regulators, e.g., to control flow rate, valves, fluid reservoirs, resistors, filters, conduits, lines, tubes and/or hoses. The conduits, lines, tubes, or hoses may be flexible or rigid. For example, a flexible line may be connected to device 20 to deliver fluid and/or remove fluid, thereby allowing device 20 to be easily manipulated by a surgeon. Fluid reservoirs may include an IV bag or bottle, for example.

Fluid source 40 may be incorporated into tissue-engaging device 20, thereby delivering fluid or removing fluid at the target tissue site. Fluid source 40 may be slaved to tissue-engaging device 20, suction source 30, energy source 50, sensor 60 and/or processor 70. For example, fluid source 40 may be designed to automatically stop or start the delivery of fluid while tissue-engaging device 20 is engaged with tissue. Fluid source 40 may be slaved to a robotic system or a robotic system may be slaved to fluid source 40.

Fluid source 40 may comprise one or more switches, e.g., a surgeon-controlled switch. One or more switches may be incorporated in or on fluid source 40 or any other location easily and quickly accessed by the surgeon for regulation of fluid delivery by the surgeon. A switch may be, for example, a hand switch, a foot switch, or a voice-activated switch comprising voice-recognition technologies. A switch may be physically wired to fluid source 40 or it may be a remote control switch. Fluid source 40 and/or system 10 may include a visual and/or audible signal used to alert a surgeon to any change in the delivery of fluid. For example, a beeping tone or flashing light may be used to alert the surgeon that a change has occurred in the delivery of fluid.

Fluids delivered to tissue-engaging device 20 may include saline, e.g., normal, hypotonic or hypertonic saline, Ringer's solution, ionic, contrast, blood, and/or energy-conducting liquids. An ionic fluid may electrically tissue-engaging device 20 to tissue thereby lowering the impedance at the target tissue site. An ionic irrigating fluid may create a larger effective electrode surface. An irrigating fluid may cool the surface of tissue thereby preventing over heating or cooking of tissue which can cause popping, desiccation, and charring of tissue. A hypotonic irrigating fluid may be used to electrically insulate a region of tissue. Fluids delivered to tissue-engaging device 20 may include gases, adhesive agents and/or release agents.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered with a fluid. Biological agents may be found in nature (naturally occurring) or may be chemically synthesized. Cells and cell components, e.g., mammalian and/or bacterial cells, may be delivered with a fluid.

One or more of a variety of pharmacological agents, biological agents and/or drugs may be delivered or administered to a patient, for a variety of functions and purposes as described below, prior to a medical procedure, intermittently during a medical procedure, continuously during a medical procedure and/or following a medical procedure. For example, one or more of a variety of pharmacological agents, biological agents and/or drugs, as discussed above and below, may be delivered before, with or after the delivery of a fluid.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered as one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, system 10 may include a drug delivery device (not shown). The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as nerve stimulation electrodes or as cardiac stimulation electrodes.

A drug delivery device may be incorporated into tissue-engaging device 20, thereby delivering drugs at or adjacent the target tissue site or the drug delivery device may be placed or used at a location differing from the location of tissue-engaging device 20. For example, a drug delivery device may be placed in contact with the inside surface of a patient's heart while tissue-engaging device 20 is placed or used on the outside surface of the patient's heart.

The drug delivery device may be slaved to tissue-engaging device 20, suction source 30, fluid source 40, energy source 50, sensor 60 and/or processor 70. For example, a drug delivery device may be designed to automatically stop or start the delivery of drugs during tissue engagement of tissue-engaging device 20. The drug delivery device may be slaved to a robotic system or a robotic system may be slaved to the drug delivery device.

The drug delivery device may comprise one or more switches, e.g., a surgeon-controlled switch. One or more switches may be incorporated in or on the drug delivery device or any other location easily and quickly accessed by the surgeon for regulation of drug delivery by the surgeon. A switch may be, for example, a hand switch, a foot switch, or a voice-activated switch comprising voice-recognition technologies. A switch may be physically wired to the drug delivery device or it may be a remote control switch. The drug delivery device and/or system 10 may include a visual and/or audible signal used to alert a surgeon to any change in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

The drug delivery device may include a vasodilative delivery component and/or a vasoconstrictive delivery component. Both delivery components may be any suitable means for delivering vasodilative and/or vasoconstrictive drugs to a site of a medical procedure. For example, the drug delivery device may be a system for delivering a vasodilative spray and/or a vasoconstrictive spray. The drug delivery device may be a system for delivering a vasodilative cream and/or a vasoconstrictive cream. The drug delivery device may be a system for delivering any vasodilative formulation such as an ointment or medicament etc. and/or any vasoconstrictive formulation such as an ointment or medicament etc. or any combination thereof.

The drug delivery device may comprise a catheter, such as a drug delivery catheter or a guide catheter, for delivering a vasodilative substance followed by a vasoconstrictive substance. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. In one embodiment, one catheter may be used to deliver both a vasodilative component and a vasoconstrictive component. The drug delivery device may be a patch, such as a transepicardial patch that slowly releases drugs directly into the myocardium, a cannula, a pump and/or a hypodermic needle and syringe assembly. The drug delivery device may be an iontophoretic drug delivery device placed on the heart.

A vasodilative component may comprise one or more vasodilative drugs in any suitable formulation or combination. Examples of vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine D1-like receptor agonist, stimulant or activator. The vasodilative component may include a pharmaceutically acceptable carrier or solution in an appropriate dosage.

A vasoconstrictive component may comprise one or more suitable vasoconstrictive drugs in any suitable formulation or combination. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator. The vasoconstrictive component may include a pharmaceutically acceptable carrier or solution in an appropriate dosage System 10 may include energy source 50. Energy source 50 may comprise a control unit. Tissue-engaging device 20 may be permanently or non-permanently attached to energy source 50. Energy source 50 may supply electrical energy, radiofrequency (RF) energy, laser energy, thermal energy, microwave energy, ultrasound energy and/or any other appropriate type of energy that may be used for the desired medical procedure, for example to ablate tissue. Energy source 50 may be powered by AC current, DC current or it may be battery powered either by a disposable or re-chargeable battery. Energy source 50 may be used to coordinate the various elements of system 10. For example, energy source 50 may be configured to synchronize activation and deactivation of suction source 20 with the delivery of energy.

Energy source 50 may incorporate a controller or processor. For example, the controller may process sensed information from a sensor. The controller may store and/or process such information before, during and/or after a medical procedure. For example, the patient's tissue temperature may be sensed, stored and processed prior to and during a medical procedure.

Energy source 50 may be used to control the energy supplied to one or more energy transfer elements of tissue-engaging device 20. Energy source 50 may also gather and process information from one or more sensors. This information may be used to adjust energy levels and times. Energy source 50 may incorporate one or more switches to facilitate regulation of the various system components by the surgeon. One example of such a switch is a foot pedal. A switch may also be, for example, a hand switch, or a voice-activated switch comprising voice-recognition technologies. A switch may be physically wired to energy source 50 or it may be a remote control switch. A switch may be incorporated in or on one of the surgeon's instruments, such as surgical site retractor, e.g., a sternal or rib retractor, tissue-engaging device 20, or any other location easily and quickly accessed by the surgeon. Energy source 50 may also include a display. Energy source 50 may also include other means of indicating the status of various components to the surgeon such as a numerical display, gauges, a monitor display or audio feedback.

Energy source 50 may incorporate a cardiac stimulator and/or cardiac monitor. For example, electrodes used to stimulate or monitor the heart may be incorporated into tissue-engaging device 20. Energy source 50 may comprise a surgeon-controlled switch for cardiac stimulation or monitoring, as discussed earlier. Cardiac stimulation may comprise cardiac pacing and/or cardiac defibrillation. Energy source 50 may incorporate a cardiac mapping device for mapping the electrical signals of the heart.

A visual and/or audible signal used to alert a surgeon to the completion or resumption of energy delivery, suction, sensing, monitoring, stimulation and/or delivery of fluids, drugs and/or cells may be incorporated into energy source 50. For example, a beeping tone or flashing light that increases in frequency as the energy delivered increases.

System 10 may include sensor 60. Sensor 60 may be incorporated into tissue-engaging device 20 or it may be incorporated into a separate device. A separate sensor device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof.

Sensor 60 may comprise one or more switches, e.g., a surgeon-controlled switch. One or more switches may be incorporated in or on a sensor device or any other location easily and quickly accessed by the surgeon for regulation of sensor 60 by the surgeon. A switch may be, for example, a hand switch, a foot switch, or a voice-activated switch comprising voice-recognition technologies. A switch may be physically wired to sensor 60 or it may be a remote control switch.

Sensor 60 may include a visual and/or audible signal used to alert a surgeon to any change in the measured parameter, for example, tissue temperature, cardiac hemodynamics or ischemia. A beeping tone or flashing light may be used to alert the surgeon that a change has occurred in the parameter sensed.

Sensor 60 may comprise one or more temperature-sensitive elements, such as a thermocouple, to allow a surgeon to monitor temperature changes of a patient's tissue. Alternatively, sensor 60 may sense and/or monitor voltage, amperage, wattage and/or impedance. For example, an ECG sensor may allow a surgeon to monitor the hemodynamics of a patient during a heart positioning procedure. The heart may become hemodynamically compromised during positioning and while in a non-physiological position. Alternatively, sensor 60 may be any suitable blood gas sensor for measuring the concentration or saturation of a gas in the blood or tissues. For example, sensor 60 may be a sensor for measuring the concentration or saturation of oxygen or carbon dioxide in the blood or tissues. Alternatively, sensor 60 may be any suitable sensor for measuring blood pressure or flow, for example a Doppler ultrasound sensor system, or a sensor for measuring hematocrit (HCT) levels.

Alternatively sensor 60 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

Sensor 60 may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

Sensor 60 may be used to detect naturally detectable properties representative of one or more characteristics, e.g., chemical, physical, mechanical, thermal, electrical or physiological, of system 10 and/or a patient's bodily tissues or fluids. For example, naturally detectable properties of patient's bodily tissues or fluids may include pH, fluid flow, electrical current, impedance, temperature, pressure, tension, components of metabolic processes, chemical concentrations, for example, the absence or presence of specific peptides, proteins, enzymes, gases, ions, etc. Naturally detectable properties of system 10 may include, for example, pressure, tension, stretch, fluid flow, electrical, mechanical, chemical and/or thermal. For example, sensor 60 may be used to sense, monitor and/or control suction or vacuum delivered from suction source 30. Sensor 60 may be used to measure suction between device 20 and tissue. Sensor 60 may be used to sense, monitor and/or control fluid delivered from fluid source 40. Sensor 60 may be used to sense, monitor and/or control energy delivered from energy source 50.

Sensor 60 may include one or more imaging systems, camera systems operating in UV, visible, or IR range; electrical sensors; voltage sensors; current sensors; piezo-electric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor.

Sensor 60 may be incorporated into tissue-engaging device 20 or sensor 60 may be placed or used at a location differing from the location of tissue-engaging device 20. For example, sensor 60 may be placed in contact with the inside surface of a patient's heart while tissue-engaging device 20 is placed or used on the outside surface of the patient's heart.

Tissue-engaging device 20, suction source 30, fluid source 40, energy source 50 and/or processor 70 may be slaved to sensor 60. For example, tissue-engaging device 20 may be designed to automatically adjust suction if sensor 60 measures a predetermined sensor value, e.g., a particular suction value.

Sensor 60 may include a visual and/or audible signal used to alert a surgeon to any change in the one or more characteristics the sensor is sensing and/or monitoring. For example, a beeping tone or flashing light that increases in frequency as tissue temperature rises may be used to alert the surgeon.

System 10 may include processor 70. Processor 70 may receive and preferably interpret the signal from sensor 60. Processor 70 may comprise software and/or hardware. Processor 70 may comprise fuzzy logic. A suitable amplifier may amplify signals from sensor 60 before reaching processor 70. The amplifier may be incorporated into processor 70. Alternatively the amplifier may be incorporated into sensor 60 or tissue-engaging device 20. Alternatively, the amplifier may be a separate device. Processor 70 may be a device separate from tissue-engaging device 20, suction source 30, fluid source 40, energy source 50 or sensor 60. Processor 70 may be incorporated into tissue-engaging device 20, suction source 30, fluid source 40, energy source 50 or sensor 60. Processor 70 may control the energy delivered from the energy source 50. For example, a signal of a first intensity from sensor 60 may indicate that the energy level from energy source 50 should be lowered; a signal of a different intensity may indicate that energy source 50 should be turned off. Preferably, processor 70 may be configured so that it may automatically raise or lower the suction delivered to device 20 from suction source 30, the fluids delivered to device 20 from fluid source 40 and/or the energy delivered to device 20 from energy source 50. Alternatively, the control of suction source 30, fluid source 40 and/or energy source 50 based on output from processor 70 may be manual.

Processor 70 may include a visual display or monitor, such as, for example, a LCD or CRT monitor, to display various amounts and types of information. By software control, the user may choose to display the information in a number of ways. The monitor may show, for example, a currently sensed parameter, e.g., temperature. The monitor may also lock and display the maximum sensed value achieved. Sensed information may be displayed to the user in any suitable manner, such as for example, displaying a virtual representation of tissue-engaging device 20 on the monitor.

Alternatively, the monitor may display the voltage corresponding to the signal emitted from sensor 60. This signal corresponds in turn to the intensity of a sensed parameter at the target tissue site. Therefore a voltage level of 2 would indicate that the tissue was, for example, hotter than when the voltage level was 1. In this example, a user would monitor the voltage level and, if it exceeded a certain value, would turn off or adjust the energy source 50.

The display of processor 70 may alternatively be located on tissue-engaging device 20, suction source 30, fluid source 40, energy source 50 and/or sensor 60. An indicator, such as an LED light, may be permanently or removeably incorporated into tissue-engaging device 20, suction source 30, fluid source 40, energy source 50 and/or sensor 60. The indicator may receive a signal from sensor 60 indicating that the tissue had reached an appropriate value, for example temperature. In response, the indicator may turn on, change color, grow brighter or change in any suitable manner to indicate that the flow of energy from energy source 50 should be modified or halted. The indicator may also be located on tissue-engaging device 20, suction source 30, fluid source 40, energy source 50, sensor 60 and/or may be located on another location visible to the user.

Alternatively, the processor 70 may include an audio device that indicates to the user that the delivery of suction, fluids and/or energy should be halted or adjusted. Such an audio device may be, for example, a speaker that broadcasts a sound (for example, a beep) that increases in intensity, frequency or tone as a parameter sensed by sensor 60 increases. The user may adjust, for example, turn down or turn off energy source 50 when the sound emitted reaches a given volume or level. In another embodiment, the audio device may also give an audible signal (such as the message "turn off energy source"), for example, when a parameter sensed by sensor 60 reaches a certain level. Such an audio device may be located on tissue-engaging device 20, suction source 30, fluid source 40, energy source 50 and/or sensor 60. The audio device may also be a separate device.

Processor 70 may comprise one or more switches, e.g., a surgeon-controlled switch. One or more switches may be incorporated in or on processor 70 or any other location easily and quickly accessed by the surgeon for regulation of processor 70 by the surgeon. A switch may be, for example, a hand switch, a foot switch, or a voice-activated switch comprising voice-recognition technologies. A switch may be physically wired to processor 70 or it may be a remote control switch.

In one embodiment of the present invention, system 10 may include an illumination device (not shown). The illumination device may comprise one or more light sources and/or illuminating materials, e.g., glow-in-the-dark materials. For example, the tissue-engaging head of device 20 may comprise one or more glow-in-the-dark materials. The illumination device may be based on fluorescence technologies. The illumination device may comprise fiber optic technologies; for example a fiber optic conduit may deliver light from a remote light source to an area adjacent tissue-engaging device 20 for illumination of a surgical site.

The illumination device may comprise a light pipe, for example, to illuminate the tissue-engaging head of device 20 and/or the surgical field adjacent device 20. A transparent, semi-transparent or translucent tissue-engaging head may be illuminated merely by placement of the end of a light pipe or other light source adjacent the tissue-engaging head of device 20.

The illumination source may be powered by AC current, DC current, or it may be battery powered either by a disposable or re-chargeable battery. The illumination source may provide UV, IR and/or visible light. The illumination source may be a laser. The illumination device may be incorporated into tissue-engaging device 20 or it may be incorporated into a separate device. A separate illumination device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof.

The illumination device may comprise one or more switches, e.g., a surgeon-controlled switch. One or more switches may be incorporated in or on the illumination device or any other location easily and quickly accessed by the surgeon for regulation of the illumination device by the surgeon. A switch may be, for example, a hand switch, a foot switch, or a voice-activated switch comprising voice-recognition technologies. A switch may be physically wired to the illumination device or it may be a remote control switch.

Tissue-engaging device 20, suction source 30, fluid source 40, energy source 50, sensor 60, processor 70, drug delivery device and/or illumination device may be slaved to a robotic system or a robotic system may be slaved to tissue-engaging device 20, suction source 30, fluid source 40, energy source 50, sensor 60, processor 70, drug delivery device and/or illumination device. Computer- and voice-controlled robotic systems that position and maneuver endoscopes and/or other surgical instruments for performing microsurgical procedures through small incisions may be used by the surgeon to perform precise and delicate maneuvers. These robotic systems may allow the surgeon to perform a variety of microsurgical procedures. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

A medical procedure wherein system 10 may be used may be non-invasive, minimally invasive and/or invasive. The medical procedure may entail a port-access approach, a partially or totally endoscopic approach, a sternotomy approach or a thoracotomy approach. The medical procedure may include the use of various robotic or imaging systems. The medical procedure may be surgery on the heart. Alternatively, the medical procedure may be surgery performed on another organ of the body.

The term "medical procedure" may mean any one or more medical or surgical procedures such as, for example cardiac surgery, performed with or without cardiopulmonary bypass (CPB) circuits, heart valve repair, heart valve replacement, MAZE procedures, transmyocardial revascularization (TMR), CABG procedures, anastomosis procedures, non-surgical procedures, endoscopic procedures, non-invasive procedures, invasive procedures, port-access procedures, fluoroscopic procedures, beating heart surgery, vascular surgery, neurosurgery, electrophysiology procedures, diagnostic and therapeutic procedures, ablation procedures, ablation of arrhythmias, endovascular procedures, treatment of one or more organs and/or vessels, treatment of the heart, aneurysm repair, aortic aneurysm repairs, imaging procedures of the heart and great vessels, CAT scan procedures, MRI procedures, cardiograms, pharmacological therapies, drug delivery procedures, delivery of biological agents, gene therapies, cellular therapies, cancer therapies, radiation therapies, genetic, cellular, tissue and/or organ manipulation or transplantation procedures, coronary angioplasty procedures, placement or delivery of coated or noncoated stents, LVAD procedures, lead placement procedures, placement of cardiac reinforcement devices, placement of cardiac assistance devices, atherectomy procedures, atherosclerotic plaque manipulation and/or removal procedures, emergency procedures, cosmetic procedures, reconstructive surgical procedures, biopsy procedures, autopsy procedures, surgical training procedures, birthing procedures, congenital repair procedures, and medical procedures that require positioning one or more organs and/or tissues.

Figure 28:
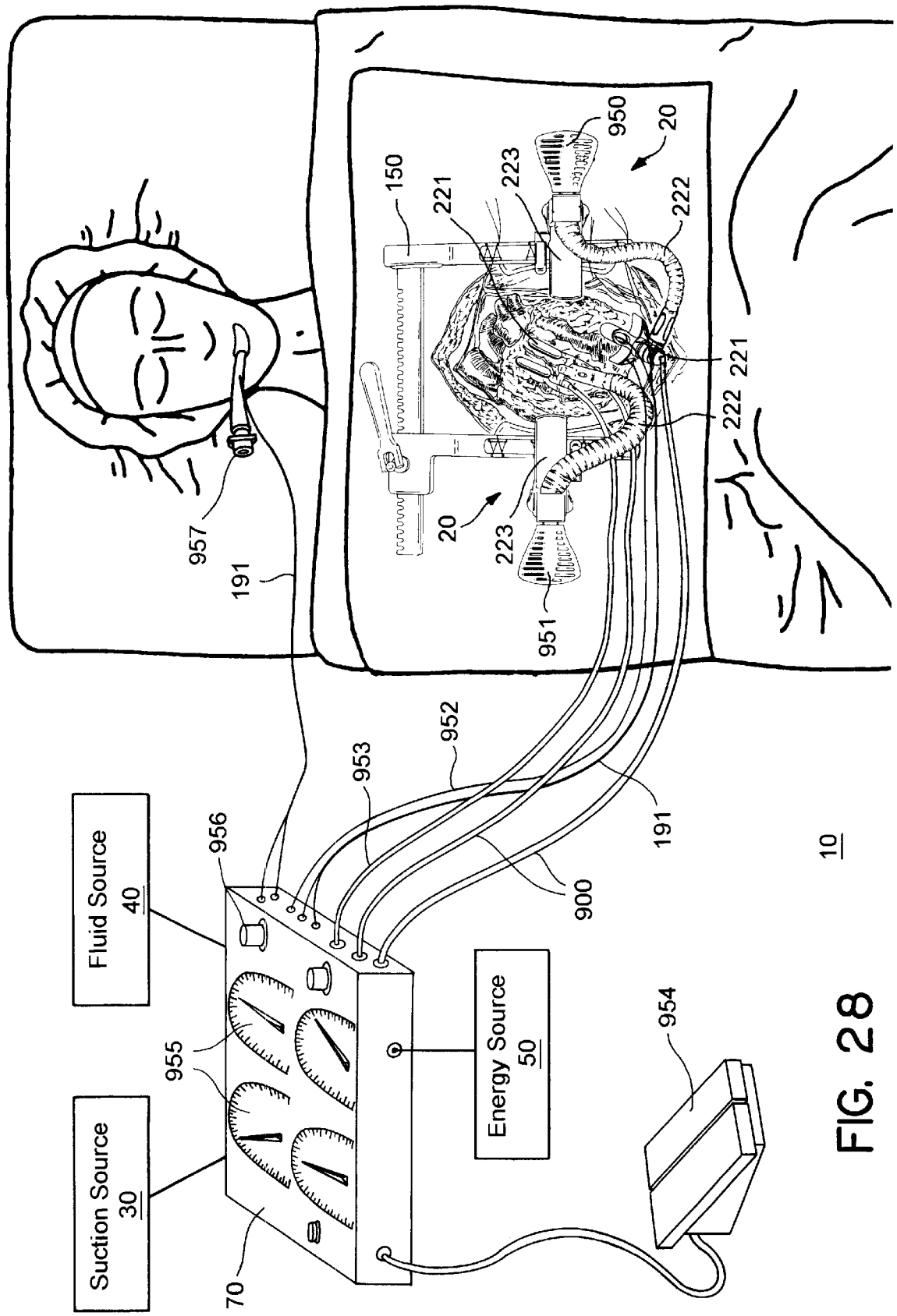
FIG. 28 is an illustration of one embodiment of a system in accordance with the present invention.

In one embodiment of the present invention, as shown in FIG. 28, system 10 includes multiple tissue-engaging devices 20 each comprising a tissue-engaging head 221, an articulating support arm 222 and a mounting clamp 223. Both devices 20 are coupled to a suction source 30 that provides a negative pressure of about 400 mm Hg. In this embodiment, suction source 30 is shown coupled to processor 70. In this embodiment, both tissue-engaging devices 20 are clamped to retractor 150 that is fixed to a patient's chest. The head of the first device 20 is placed on the apex or left ventricle of the patient's heart. Suction is provided to the first tissue-engaging device via tubing 900. The head of the first device 20 is allowed to firmly engage or grasp the surface of the heart. The heart is positioned into the desired orientation. For example, the heart may be positioned for providing access to lateral and/or posterior vessels of the heart. Articulating arm 222 of the first device 20 is locked into position when the heart is in the desired orientation via knob 950 thereby positioning and supporting the heart. In this embodiment, the head of the second device 20 is placed on the surface of the patient's heart adjacent a coronary artery. Suction is provided to the second tissue-engaging device via tubing 900. The head of the second device 20 is allowed to firmly engage or grasp the surface of the heart. Articulating arm 222 of the second device 20 is locked into position via knob 951 thereby immobilizing the area of tissue adjacent the head of the second device 20.

As shown in FIG. 28, tissue-engaging head of first device 20 may comprise one or more electrodes connected via leads 191 to energy source 50. In this embodiment, energy source 50 is shown coupled to processor 70. The electrodes may be used for pacing and/or defibrillation of the patient's heart. Tissue-engaging head of first device 20 may also comprise one or more sensors for sensing the patient's ECG, for example, connected to processor 70 via conductor 952. Second device 20 may comprise one or more fluid openings for delivery of fluid from fluid source 40. Fluid source 40 is coupled to second device 20 via tubing 953. In this embodiment, fluid source 40 is shown coupled to processor 70. As shown in this embodiment of the present invention, processor 70 is coupled to a manual foot switch 954. In addition, processor 70 comprises multiple displays 955 and knobs 956 for providing feedback and control.

As shown in FIG. 28, endotracheal tube 957 comprising one or more electrodes may be positioned in a patient's trachea. Endotracheal tube 957 may be connected to a breathing regulator (not shown in FIG. 28). The electrodes of endotracheal tube 957 may be used to stimulate the patient's vagal nerve thereby slowing or stopping the patient's heart. The patient may be given drugs as described above to help stop the beating of the heart and/or to prevent "escape" beats. Following vagal stimulation, the heart may be paced via first device 20. The electrodes of endotracheal tube 957 may be coupled to processor 70 and energy source 50 via leads 191.

In one embodiment of the present invention, a nerve stimulator may be used to electrically manipulate cardiac rhythm by stimulating the vagus nerve. This vagal stimulation may produce asystole (slowing or stopping of the heart's beating.) Once this induced asystole is stopped, i.e. once the vagal stimulation is stopped, the heart may be allowed to return to its usual cardiac rhythm. Alternatively, the heart may be paced, thereby maintaining a normal cardiac output. Vagal stimulation, alone or in combination with electrical pacing, may be used selectively and intermittently to allow a surgeon to perform a medical procedure, such as a CABG procedure, and yet still allow the heart itself to supply blood circulation to the body while one or more tissue-engaging devices 20 are used to position and/or stabilize an area of the heart. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers", Dec. 21, 1999, to Hill and Junkman and in U.S. patent application Ser. No. 09/670,441 filed Sep. 26, 2000, Ser. No. 09/669,960 filed Sep. 26, 2000, Ser. No. 09/670,370 filed Sep. 26, 2000, Ser. No. 09/669,961 filed Sep. 26, 2000, Ser. No. 09/669,355 filed Sep. 26, 2000 and Ser. No. 09/670,369 filed Sep. 26, 2000. These patents and patent applications are assigned to Medtronic, Inc. and are incorporated herein by reference.

Figure 29:
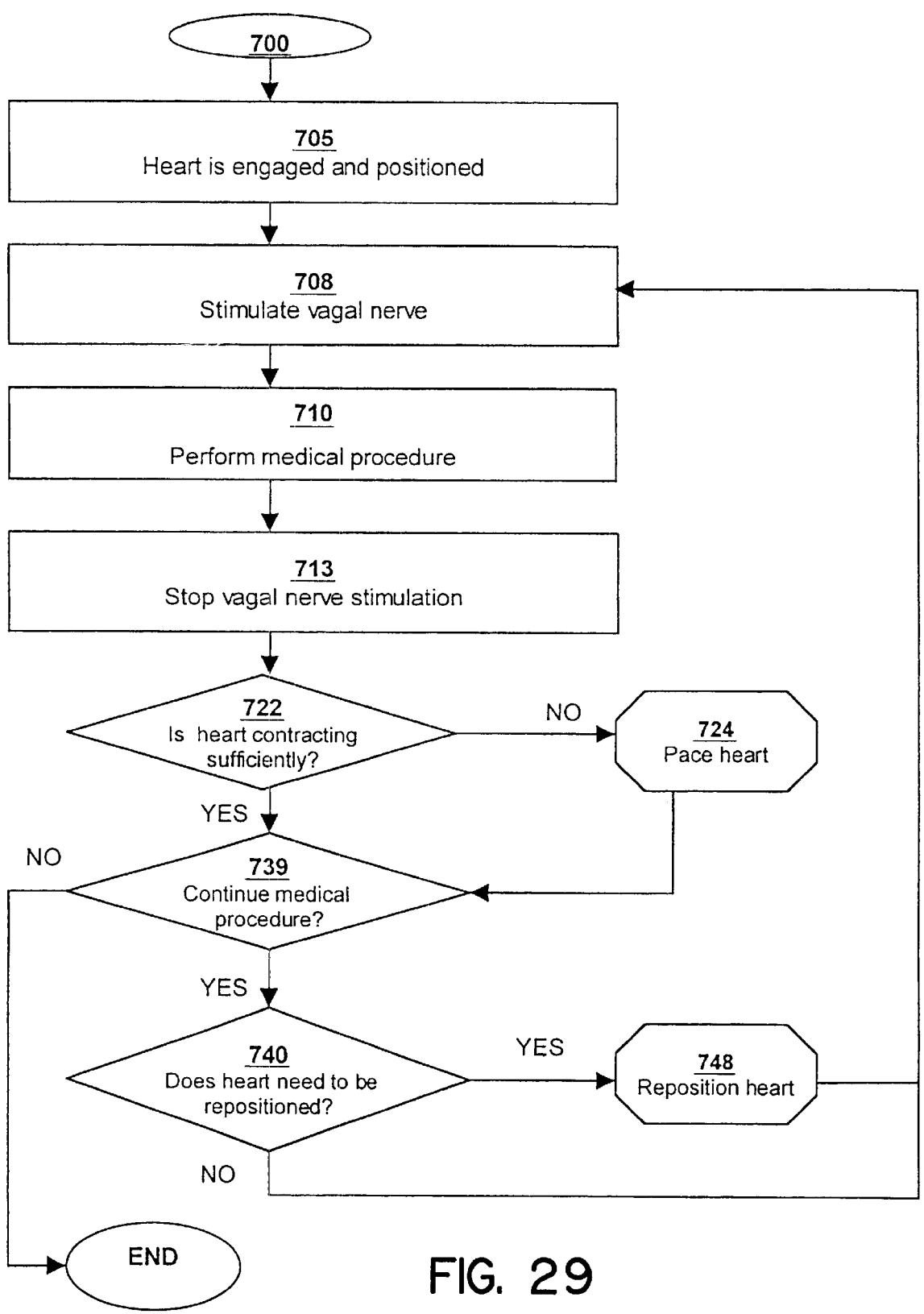
FIG. 29 is a flow diagram of one embodiment of the present invention.

FIG. 29 shows a flow diagram of one embodiment of the present invention. The patient is prepared for a medical procedure at 700. Once the patient is prepared, the heart is engaged and positioned using tissue-engaging device 20 of system 10 (Block 705). Once the heart is positioned in a desired orientation, a nerve that controls the beating of the heart is stimulated to slow down or stop the contractions of the heart (Block 708). Such a nerve may be for example a vagal nerve. During this time, one or more of a variety of pharmacological agents or drugs may be delivered to the patient. These drugs may produce reversible asystole of a heart while maintaining the ability of the heart to be electrically paced. Other drugs may be administered for a variety of functions and purposes as described above. Drugs may be administered at the beginning of the procedure, intermittently during the procedure, continuously during the procedure or following the procedure.

Typically, vagal nerve stimulation prevents the heart from contracting. This non-contraction must then be followed by periods without vagal nerve stimulation during which the heart is allowed to contract, and blood flow is restored throughout the body. Following initial slowing or stopping of the heart, a medical procedure, e.g., CABG, ablation, lead placement and/or other procedure as described above, is begun (Block 710). Following a brief interval of nerve stimulation while a medical procedure is performed, nerve stimulation is ceased (Block 713) and the heart is allowed to contract. A cardiac stimulator or pacemaker may be used to cause the heart to contract or the heart may be free to beat on its own (Blocks 722 and 724). In one embodiment of the present invention, tissue-engaging device 20 includes one or more electrodes, which may be used for pacing, coupled to energy source 50. Processor 70 may control both cardiac and nerve stimulation. For example, processor 70 may automatically proceed to block 713 to cease nerve stimulation. In addition, processor 70 may automatically begin cardiac stimulation. If the medical procedure needs to continue or a new medical procedure is to be performed, the heart may be repositioned if necessary or desired at Block 748.

Figure 30:
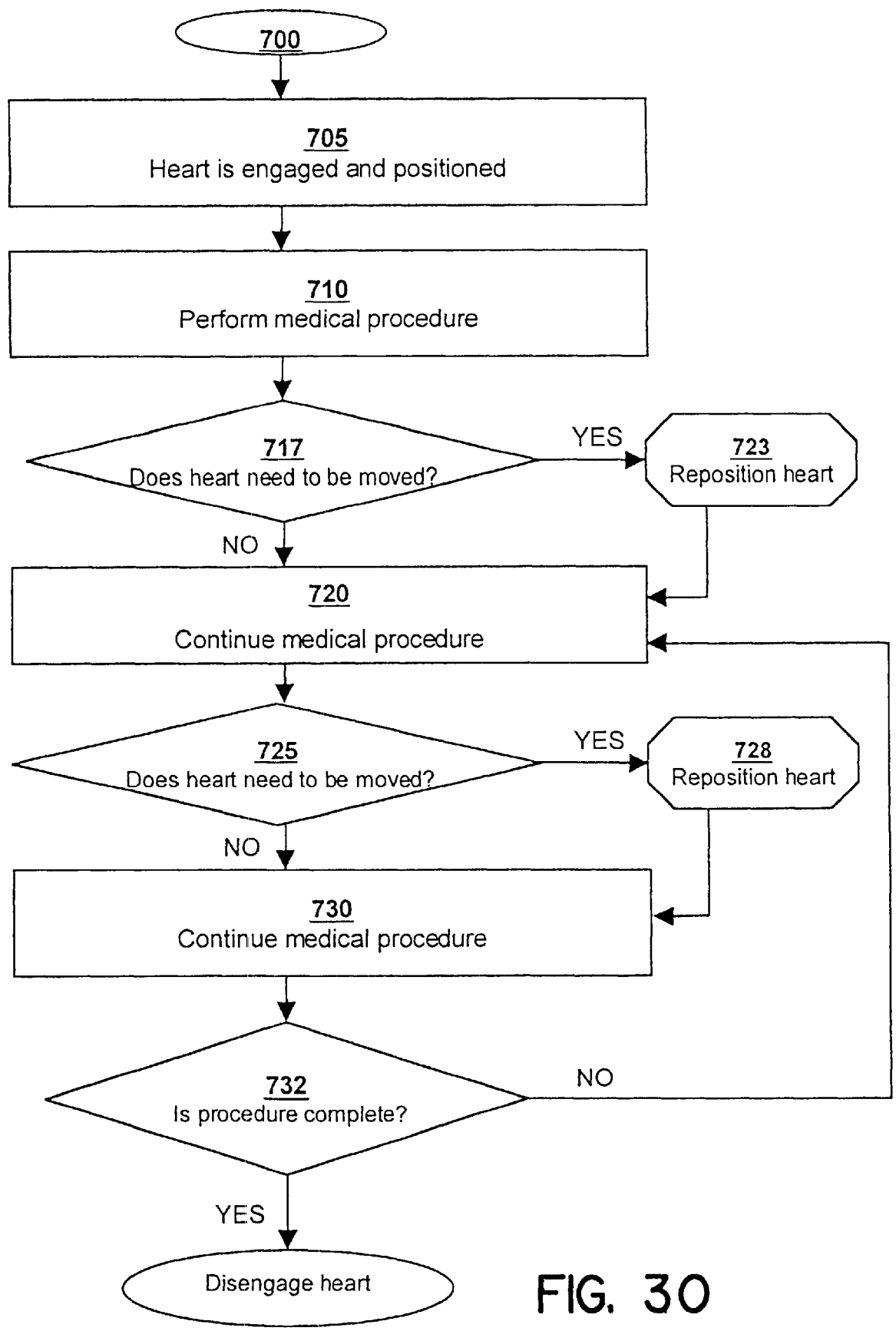
FIG. 30 is a flow diagram of one embodiment of the present invention.

FIG. 30 shows a flow diagram of one embodiment of the present invention. The patient is prepared for a medical procedure at 700. At this point, the heart may be engaged and positioned by tissue-engaging device 20 of system 10, for example, to provide access to the posterior or backside of the heart (Block 705). As seen in FIG. 29, heart positioning may occur throughout the entire procedure in a continuous or intermittent manner. At Block 710, a medical procedure, e.g., a CABG procedure comprising the use of a distal anastomotic device or other medical procedure as mentioned above, is begun. At Block 717, it is determined if the heart needs to be repositioned. For example, upon completion of a first anastomosis, e.g., via delivery of a distal anastomotic device, the heart may be repositioned to provide better access for creation of a second anastomosis. Again at Block 725, it is determined if the heart needs to be repositioned. For example, upon completion of a second anastomosis, e.g., via delivery of a distal anastomotic device, the heart may again be repositioned to provide access for creation of a third anastomosis. During the medical procedure fluids may be delivered to tissue-engaging device 20 from fluid source 40. Processor 70 may control the delivery of fluids from fluid source 40.

Figure 31:
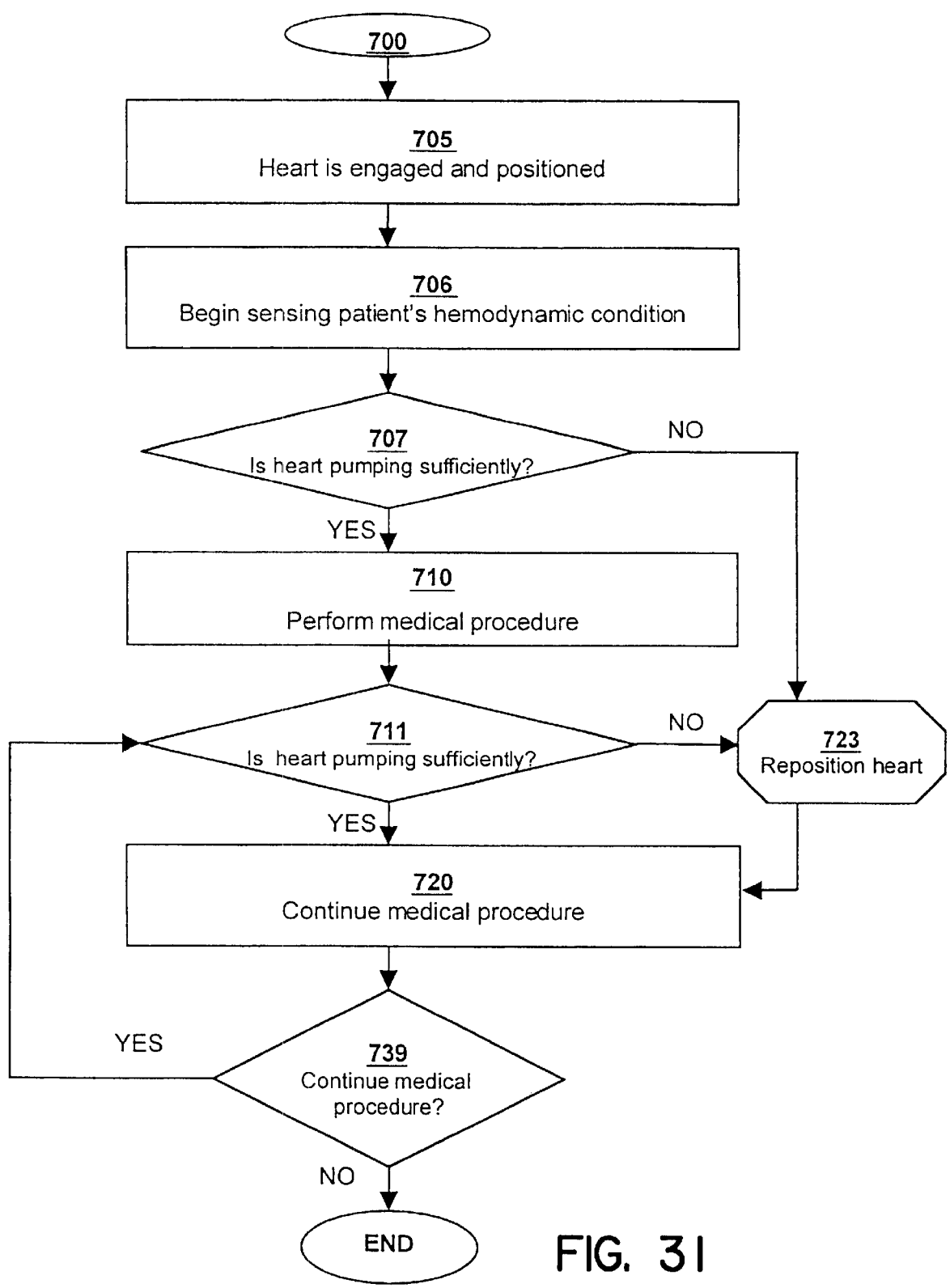
FIG. 31 is a flow diagram of one embodiment of the present invention.

FIG. 31 shows a flow diagram of one embodiment of the present invention. The patient is prepared for a medical procedure at 700. At this point, the heart may be engaged and positioned by tissue-engaging device 20 of system 10, for example, to provide access to the posterior or backside of the heart (Block 705). As seen in FIG. 29, heart positioning may occur throughout the entire procedure in a continuous or intermittent manner. At Block 706, the patient's hemodynamic condition may be sensed and monitored, for example, the patient's ECG may be sensed and monitored by sensor 60 and processor 70. At Block 707, it is determined if the heart needs to be repositioned. Following repositioning of the heart (Block 723), if necessary, a medical procedure is performed at Block 710. The medical procedure, e.g., a CABG procedure comprising the use of a distal anastomotic device or other medical procedure as mentioned above, is begun. At Block 711, it is again determined if the heart needs to be repositioned. For example, upon completion of a first anastomosis, e.g., via delivery of a distal anastomotic device, the heart may be repositioned to provide better access for creation of a second anastomosis located in a different location from the first anastomosis. Following repositioning of the heart (Block 723), if necessary, the medical procedure is continued at Block 720.

System 10 may be used for creating space in a surgical field. For example, tissue-engaging device 20 may be used to grasp and position the pericardium away from the surface of the heart thereby creating space between the surface of the heart and the pericardium. This type of procedure may be termed "tenting". Tissue-engaging device 20 may be used to grasp and position a heart away from a rib cage, for example in an endoscopic procedure, thereby creating space for a surgeon to work between the heart and the rib cage. Tissue-engaging device 20 may be used to grasp and position a heart away from other adjacent or nearby organs thereby creating space for a surgeon to work.

Figure 32:
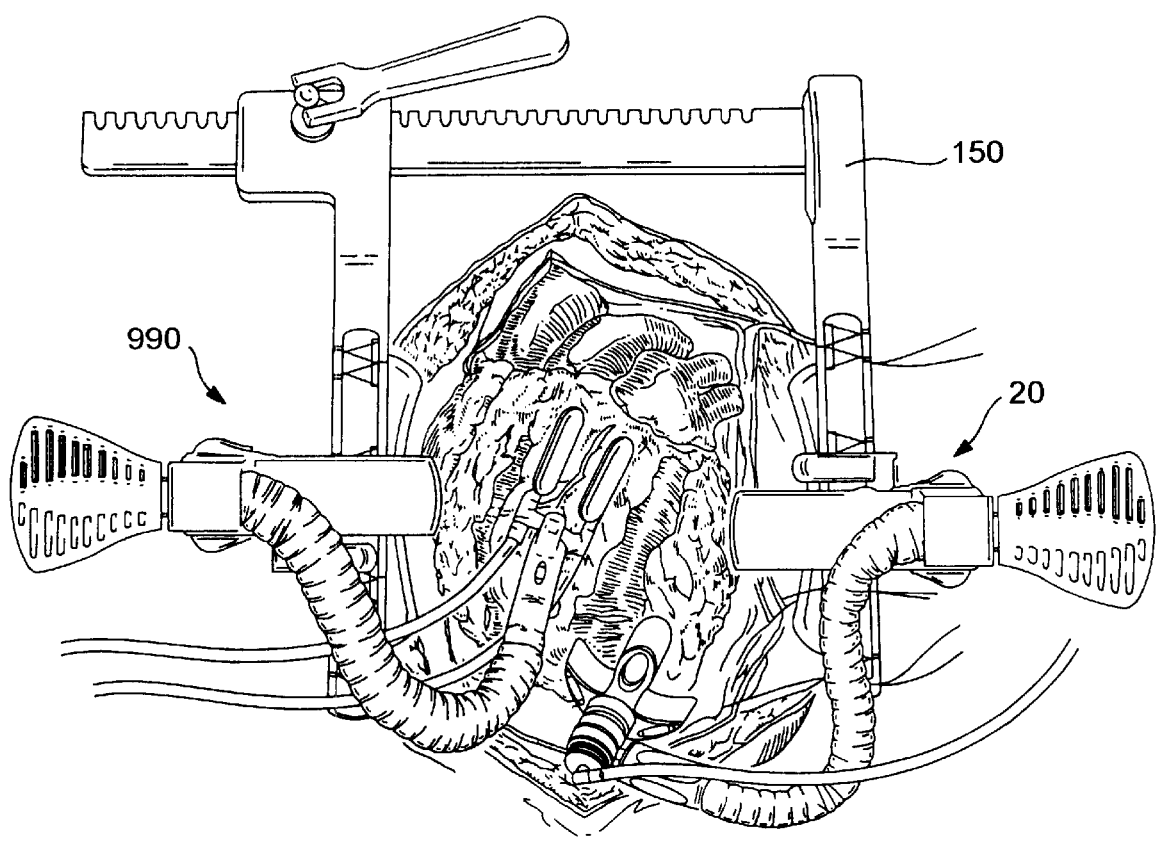
FIG. 32 is an illustration of one embodiment of a medical device in use in accordance with the present invention.

In one embodiment of the present invention, as shown in FIG. 32, the medical procedure may include the use of one or more tissue stabilization devices, e.g., the "OCTOPUS 3"™ which is marketed by Medtronic, Inc., Minneapolis, Minn. USA. See, also, tissue stabilizers disclosed in U.S. Pat. Nos. 5,836,311; 5,927,284 and 6,015,378, co-assigned U.S. patent application Ser. No. 09/396,047, filed Sep. 15, 1999; and Ser. No. 09/678,203, filed Oct. 2, 2000, and European Patent Publication No. EP 0 993 806. These patents are assigned to Medtronic, Inc. and are incorporated herein by reference. As shown in FIG. 32, tissue-engaging device 20 of system 10 may be used in a medical procedure, e.g., a CABG procedure, in combination with a tissue stabilizer 990. As shown in FIG. 32, both devices may be attached to retractor 150 fixed to a patient's chest.

Figure 33:
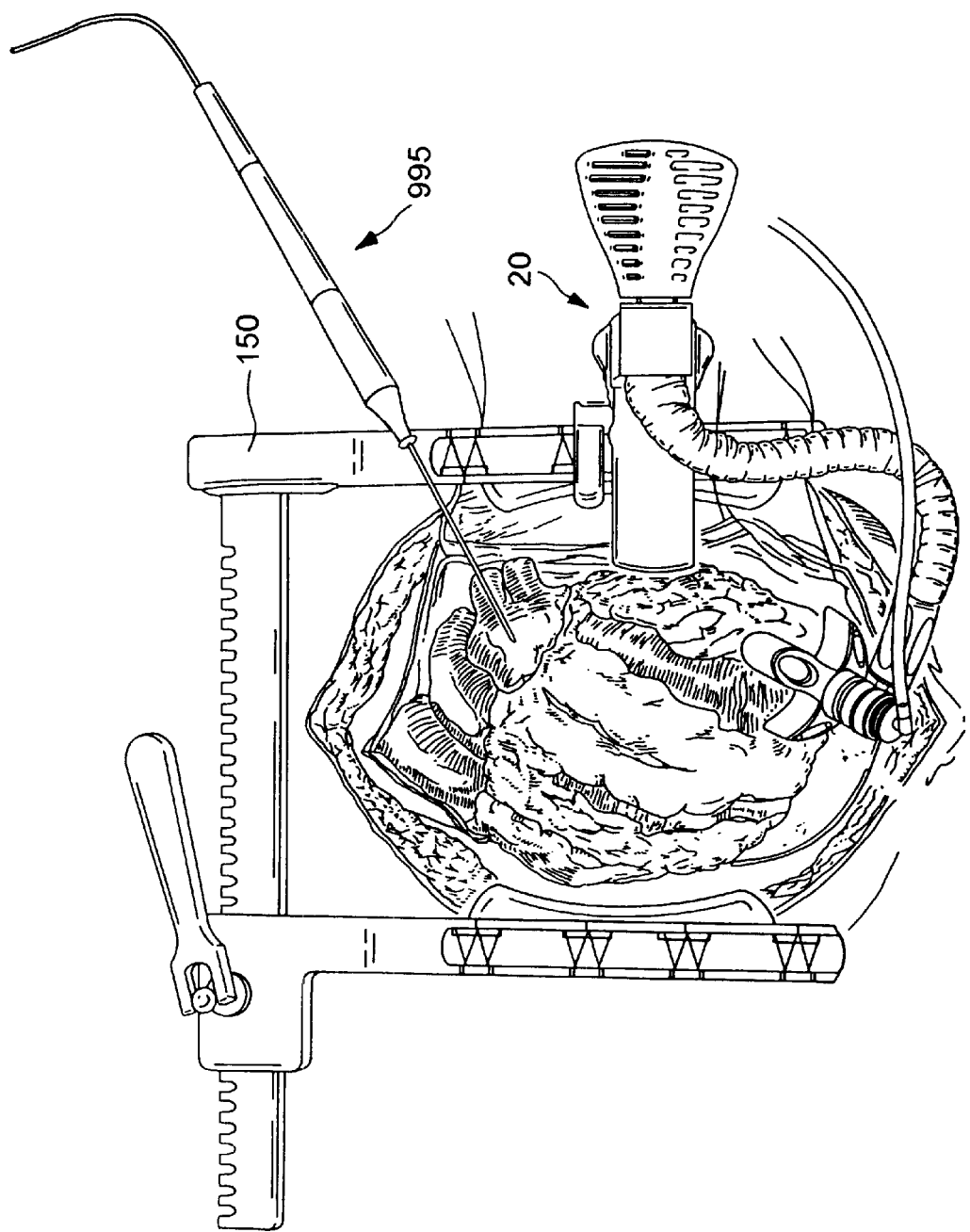
FIG. 33 is an illustration of one embodiment of a medical device in use in accordance with the present invention.

In one method of the present invention, as shown in FIG. 33, the medical procedure may include the use of one or more tissue ablation devices. For example, see tissue ablation devices disclosed in U.S. patent application Ser. No. 09/844220 filed Apr. 26, 2001, Ser. No. 09/844221 filed Apr. 26, 2001 and Ser. No. 09/843897 filed Apr. 26, 2001. These patent applications are assigned to Medtronic, Inc. and are incorporated herein by reference. As shown in FIG. 33, tissue-engaging device 20 of system 10 may be used in a medical procedure, e.g., an ablation procedure, in combination with a tissue ablation device 995. Device 20 may be attached to retractor 150 fixed to a patient's chest. Tissue ablation devices may be used to ablate tissue located within a body cavity, such as the endocardial or epicardial tissue of the heart. Other body organ tissue, such as the liver, lungs or kidney, may also be positioned and ablated. Other tissue types may be ablated including skin, muscle or even cancerous tissue or abnormal tissue growth.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of performing a medical procedure on a heart, comprising:

providing a suction assisted positioning device;

engaging the heart with the positioning device;

positioning the heart into a non-physiological orientation;

stimulating a nerve to adjust the beating of the heart to a first condition;

performing the medical procedure on the heart;

reducing stimulation of the nerve to adjust the beating of the heart to a second condition;

stimulating the nerve a subsequent time in order to re-adjust the beating of the heart to the first condition; and, continuing the medical procedure.

2. The method of claim 1 wherein the nerve is stimulated using endotracheal stimulation.

3. The method of claim 1 wherein the stimulation is stopped to achieve the second condition.

4. The method of claim 1 wherein the first condition is a stopped condition.

5. The method of claim 1 wherein the first condition is a slowed condition.

6. The method of claim 1 wherein the second condition is a beating condition.

7. The method of claim 1 further comprising:

stimulating the heart in order to adjust the beating of the heart to the second condition.

8. The method of claim 7 wherein the heart is stimulated by pacing.

9. The method of claim 1 further comprising:

administering at least one drug during the medical procedure.

10. The method of claim 9 wherein the drug is selected from the group consisting of:

a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

11. The method of claim 1 wherein the nerve is a vagal nerve.

12. The method of claim 1 wherein the medical procedure is selected from the group consisting of:

surgical procedures, CPB procedures, heart valve repair procedures, heart valve replacement procedures, MAZE procedures, TMR procedures, CABG procedures, anastomosis procedures, non-surgical procedures, endoscopic procedures, non-invasive procedures, invasive procedures, port-access procedures, fluoroscopic procedures, beating heart surgery procedures, vascular surgery procedures, neurosurgery procedures, electrophysiology procedures, diagnostic procedures, therapeutic procedures, ablation procedures, endovascular procedures, aneurysm repair procedures, imaging procedures, CAT scan procedures, MRI procedures, cardiogram procedures, pharmacological therapy procedures, drug delivery procedures, biological agent delivery procedures, gene therapy procedures, cellular therapy procedures, cancer therapy procedures, radiation therapy procedures, genetic procedures, cellular procedures, tissue manipulation procedures, organ manipulation procedures, transplantation procedures, coronary angioplasty procedures, stent placement procedures, stent delivery procedures, LVAD procedures, lead placement procedures, atherectomy procedures, atherosclerotic plaque manipulation procedures, atherosclerotic plaque removal procedures, emergency procedures, reconstructive surgery procedures, procedures including cardiac reinforcement devices, procedures including cardiac assistance devices, biopsy procedures, surgical training procedures, congenital repair procedures, and medical procedures that require positioning one or more organs and/or tissues.

13. The method of claim 1 further comprising:

positioning the heart a subsequent time into a different non-physiological orientation.

14. The method of claim 1 further comprising:

delivering one or more fluids during the medical procedure.

15. The method of claim 14 wherein the one or more fluids comprises at least one diagnostic agent, therapeutic agent or biological agent.

16. The method of claim 1 further comprising:

evaluating the hemodynamic condition of the heart with a sensor.

* * * * *